US010266564B2

(12) United States Patent
Reddy et al.

(10) Patent No.: US 10,266,564 B2
(45) Date of Patent: Apr. 23, 2019

(54) CATIONIC LIPID CORDIARIMIDE HYBRID COMPOUNDS AND A PROCESS FOR PREPARATION THEREOF

(71) Applicant: COUNCIL OF SCIENTIFIC & INDUSTRIAL RESEARCH, New Delhi (IN)

(72) Inventors: Bathula Surendar Reddy, Lucknow (IN); V.k.k. Durga Rao, Lucknow (IN); Komal Sharma, Lucknow (IN); M. Prathap Reddy, Lucknow (IN); Dibyendu Banerjee, Lucknow (IN); Deependra Kumar Singh, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 15/317,294

(22) PCT Filed: Jun. 10, 2015

(86) PCT No.: PCT/IN2015/000235
§ 371 (c)(1),
(2) Date: Dec. 8, 2016

(87) PCT Pub. No.: WO2015/189856
PCT Pub. Date: Dec. 17, 2015

(65) Prior Publication Data
US 2017/0137462 A1 May 18, 2017

(30) Foreign Application Priority Data

Jun. 10, 2014 (IN) .......................... 1566/DEL/2014

(51) Int. Cl.
*C07D 211/88* (2006.01)
*C07K 5/06* (2006.01)
*A61P 35/00* (2006.01)
*A61K 38/00* (2006.01)

(52) U.S. Cl.
CPC .......... *C07K 5/06008* (2013.01); *A61P 35/00* (2018.01); *C07D 211/88* (2013.01); *A61K 38/00* (2013.01)

(58) Field of Classification Search
CPC .................................................... C07D 211/88
USPC .......................................... 546/220; 514/328
See application file for complete search history.

(56) References Cited

PUBLICATIONS

Golub et al, Science, vol. 286, Oct. 15, 1999, pp. 531-537.*
Simone, Oncology:Introduction, Cecil Textbook of Medicine, ed Bennett et al. W.B.Saunders CO. 20th ed, vol. 1, pp. 1004-1010. (Year: 1996).*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
International Search Report and Written Opinion for PCT/IN2015/000235 dated Sep. 16, 2016.
Muktapuram et al, "Anticancer siRNA delivery by new anticancer molecule: A novel combination strategy for cancer cell killing", European Journal of Medicinal Chemistry, vol. 56, Oct. 1, 2012, pp. 400-408.
Pal et al, "Structure-Activity Study to Develop Cationic Lipid-Conjugated Haloperidol Derivatives as a New Class of Anticancer Therapeutics", Journal of Medi ci nal Chemistry, vol. 54, No. 7, Apr. 14, 2011.
Sinha et al: "A Lipid-Modified Estrogen Derivative that Treats Breast Cancer Independent of Estrogen Receptor Expression through Simultaneous Induction of Autophagy and Apoptosis", Molecular Cancer Research, vol. 9, No. 3, Feb. 2, 2011, pp. 364-374.

\* cited by examiner

*Primary Examiner* — Patricia L Morris
(74) *Attorney, Agent, or Firm* — Fish & Richardson P.C.

(57) ABSTRACT

The present invention relates to the cationic lipid cordiaroimide hybrid compounds of formula I. The present invention provides a process for preparation of these compounds is also being elaborated. The compounds described provides anticancerous activity against cell lines including PC-3 (prostate cancer), HepG2 (liver cancer), MCF-7 (breast cancer) and NIH-1/3T3 (non cancer cells. The compound was also capable of inducing caspase-3 mediated apoptosis in HepG2 cells by arresting the cell cycle in the G1 phase. Furthermore, the compound exhibited DNA ligase I inhibition. The present class of cationic lipid cordiarimide hybrids is likely to find specific use in developing novel targeted therapies for liver and prostate cancers.

14 Claims, 9 Drawing Sheets

A) Boc anhydride,3N, NaOH, THF,H$_2$O.12 h.B) NHS, DCC, DMF, 80°c ,12 h.   C) Acetonitrile,K$_2$CO$_3$, 80°c Reflux,12 h.
D) TFA, DCM, r.t 30 mim.   E) Boc Glycine, EDCL, HOBt, Et3N, r.t   F) TFA, DCM, r.t 30 mim.
G) (CnH2n+1Br), n=(3-14), Et$_3$N, 80°C,reflux 12 h.H) Methyl iodide, DCM, r.t

CATIONIC LIPID CORDIARIMIDE HYBRID COMPOUNDS AND A PROCESS FOR PREPARATION THEREOF

FIELD OF THE INVENTION

The present invention relates to the cationic lipid-cordiarimide hybrid compounds of formula I. The present invention also relates to the process of the preparation of cationic lipid-cordiarimide hybrid compounds of formula I. The present invention further relates to the use of these compounds in cancer therapy by inducing apoptosis and the effect of these molecules on cancer cell cycle progression. The present invention also relates to use of these molecules as inhibitors of DNA ligase I.

BACKGROUND OF THE INVENTION

Cancer is a major cause of illness and death worldwide. It is the leading cause of human mortality exceeded only by cardiovascular diseases (Evangelia D. C. et. al. *Bioorg. Med. Chem.*, 2005, 13, 765-72). Cancer occurs in a wide range of tissues with different outcomes. Approximately 200 different types of cancers are reported with lung, breast, prostate and colon cancer accounting for the majority of deaths (cancer-researchuk.org). Cancer arises from an accumulation of genetic and epigenetic alterations within proto-oncogenes and tumour suppressor genes leading to the deregulation of the tightly controlled signaling pathways (Smith S. C. et. al. *Nat Rev Cancer.*, 2009, 9, 253-264; Grady W. M. et. al. *Gastroenterology*, 2008, 135, 1079-99). Abnormal signaling cascades breakdown the cell cycle and produce genomic and chromosomal instability (Malumbres M. et. al. *Nat Rev Cancer.*, 2009, 9, 153-166; Stratton M. R. et. al. *Nature.*, 2009, 458, 719-24). Subsequently, normal cells lose control over their growth and forms primary tumors. In later stages, cancerous cells metastasize from the primary tumours to distant organs in the body and it is difficult to treat the cancer at this stage (Klein C. A. et. al. *Nat Rev Cancer.*, 2009, 9, 302-12). Chemotherapy and radiation therapies are two widely used therapeutic options for the treatment of cancer. These techniques effectively block the tumor growth but traditionally prescribed chemotherapeutic agents have problems with toxicity and drug resistance (Urruticoechea A. et. al. Current Pharmaceutical Design, 2010, 16, 3-10). Although, numerous kinase inhibitors have been discovered recently and several have been successfully developed, including Gleevec, (Robert R. Jr. Biochem Biophys Res Commun, 2003, 309, 709-17) Iressa, (Nutt J. E. et. al. J. Br. J. Cancer., 2004, 8, 1679-85) Tarceva, (Dowell J. et. al. Nat. Rev. Drug Disc., 2005, 4, 13-14) and Tykerb (Moy B. et. al. Oncologist., 2006, 10, 1047-57) there is still a strong demand for discovery of more efficacious and less toxic anticancer agents. Other anti-cancer targets that have been realized recently are human DNA ligases. The potential of targeting ligases arises from the fact that they are indispensible in all DNA replication and repair processes in the body, processes that are already targeted the most in chemotherapy. Inhibiting ligases lead to accumulation of strand breaks in the cells that are lethal at high concentrations. Reports also conform that the levels of DNA ligases are higher in cancer cells compared to normal cells that do not replicate all the time. We have recently published a review citing all known ligase inhibitors and reviewed all the methods by which ligases maybe targeted and their functions maybe inhibited (Singh D. K. et. al. Med Res Rev., 2013 DOI 10.1002/med.21298).

Molecular hybridization is a new concept useful for the design and development of novel biologically active molecules. Above paradigm produce a new hybrid compounds based on the combination of pharmacophoric moieties of different bioactive substances with improved affinity and efficacy, when compared to the parent compounds (Sashidhara K. V. et. al. J. Med. Chem., 2012, 55, 2769-79). This strategy has resulted in compounds with modified selectivity profile, different and/or dual modes of action and reduced undesired side effects (Meunier B. Acc Chem Res., 2008, 41, 69-77). Cationic lipid conjugated small molecules are emerging hybrid molecules. Upon cationic lipid modifications, biologically active compounds whether natural or synthetic, show improved anticancer activities with different modes of action.

Using this lucrative lipid hybridization strategy recently various cationic lipidated small molecules with improved activity have been reported including, cationic lipid-haloperidol hybrids (Banerjee R. et. al. J. Med. Chem., 2011, 54, 2378-90) and cationic lipidated emodins (Wang et. al. Eur. J. Med. Chem., 2012, 56, 320-31). Above reports give the impression that the cationic lipid conjugation enhances anticancer activity of the small molecules but the crucial point to be noted is that the improved activity is highly dependent on the small molecule portion and that too is highly chain length specific. Here we would like to reveal an important point that not all the combinations of small molecules and carbon chain lengths associated with cationic lipids produces anticancer property, there needs to be a specific combination in order to generate potential anticancer agents. The whole picture can be explained from the example of estradiol that has strong compatibility with only eight chain length containing cationic lipid [Mol. Cancer Res., 2011, 9, 364-374], whereas benzamide has best compatibility with only ten chain length cationic moiety [Eur. J. Med. Chem., 2012, 56, 400-408] in order to elicit the selective anticancer activity. Best on the mentioned examples, one cannot simply generalize that cationic lipid moiety enhances the activity of all small molecules.

Inspired by these encouraging results, in order to further explore the structure-activity relationship (SAR) of the cationic lipid portion, we envisioned the construction of cationic lipo-cordiarimide A hybrids as shown in FIG. 1. The rationale behind the selection of 'cordiarimide A' is it is a glutarimide natural product and recently isolated from the roots of Cordia globifera (Parks J. et. al. J. Nat. Prod., 2010, 73, 992). Glutarimide's are reported to have antibacterial, antitumoral, anti-inflammatory, and other pharmacological activities (Decker S. et. al. Ann. N.Y. Acad Sci., 2005, 1059, 61-9). Thalidomide and Lenalidomide are the most well known drugs among glutarimide derivatives.

In the present invention we report the design, synthesis, anticancer activity and DNA ligase-1 inhibitory potential of novel cationic lipid modified cordiarimides.

OBJECTIVE OF THE PRESENT INVENTION

The main objective of the present invention is to provide the cationic lipid-cordiarimide hybrid compounds of formula I. Another object of the present invention is to provide a process for the preparation of cationic lipid-cordiarimide hybrid compounds of formula I. Still another objective of the present invention is to provide the effect of the cationic lipid coriarimide compounds of formula I on the biochemical processes of cancer cells including apoptosis inducing activity, cell cycle arrest and caspase activation.

Yet another objective of the present invention is to provide the selective DNA ligase I inhibitory profiles of the new cationic lipid-cordiarimide hybrid compounds of formula I.

Still another objective of the present invention is to provide the potential anticancer activities of novel cationic lipid-cordiarimide hybrid compounds of formula I, useful in the development of novel targeted cancer therapies.

SUMMARY OF THE INVENTION

Accordingly the present invention provides a cationic lipid cordiarimide hybrid compound of formula I

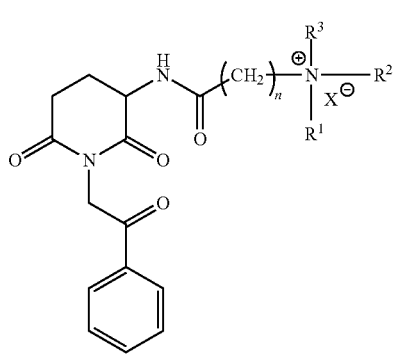

Formula I wherein,
each of $R^1$ and $R^2$ is independently hydrogen or a lipophilic moiety and $R^1$ and $R^2$ are not hydrogen at the same time.
$R^3$ is independently hydrogen or alkyl,
n is an integer between 1 and 7 and
X is optionally selected from chlorine, bromine or iodine,
wherein, lipophilic moiety is selected from the group consisting of $C_{2-22}$ alkyl, mono-, di- and tri-unsaturated alkenyl.

In an embodiment of the present invention, the representative compounds of formula I comprises:
a) {[2,6-Dioxo-1-(2-oxo-2-phenyl-ethyl)-piperidin-3-ylcarbamoyl]-methyl}-Diethyl-methyl-ammonium iodide: (8a)
b) Dipropylamm{[2,6-Dioxo-1-(2-oxo-2-phenyl-ethyl)-piperidin-3-ylcarbamoyl]-methyl}-methylammonium iodide: (8b)
c) Dibutyl-{[2,6-dioxo-1-(2-oxo-2-phenyl-ethyl)-piperidin-3-ylcarbamoyl]-methyl}-methyl-ammonium iodide: (8c)
d) {[2,6-Dioxo-1-(2-oxo-2-phenyl-ethyl)-piperidin-3-ylcarbamoyl]-methyl}-Methyl-dipentyl-ammonium iodide: (8d)
e) {[2,6-Dioxo-1-(2-oxo-2-phenyl-ethyl)-piperidin-3-ylcarbamoyl]-methyl}-Dihexyl-methyl-ammonium iodide: (8e)
f) {[2,6-Dioxo-1-(2-oxo-2-phenyl-ethyl)-piperidin-3-ylcarbamoyl]-methyl}-Diheptyl-methyl-ammonium iodide: (8f)
g) {[2,6-Dioxo-1-(2-oxo-2-phenyl-ethyl)-piperidin-3-ylcarbamoyl]-methyl}-Methyl-dioctyl-ammonium iodide: (8g)
h) {[2,6-Dioxo-1-(2-oxo-2-phenyl-ethyl)-piperidin-3-ylcarbamoyl]-methyl}-Methyl-dinonyl-ammonium iodide: (8h)
i) Bis-decyl-{[2,6-dioxo-1-(2-oxo-2-phenyl-ethyl)-piperidin-3-ylcarbamoyl]-methyl}-methyl-ammonium iodide: (8i)
j) {[2,6-Dioxo-1-(2-oxo-2-phenyl-ethyl)-piperidin-3-ylcarbamoyl]-methyl}-Methyl-diundecyl-ammonium iodide: (8j)
k) {[2,6-Dioxo-1-(2-oxo-2-phenyl-ethyl)-piperidin-3-ylcarbamoyl]-methyl}-Didodecyl-methyl-ammonium iodide: (8k)
l) {[2,6-Dioxo-1-(2-oxo-2-phenyl-ethyl)-piperidin-3-ylcarbamoyl]-methyl}-Methyl-ditridecyl-ammonium iodide: (8l)
m) {[2,6-Dioxo-1-(2-oxo-2-phenyl-ethyl)-piperidin-3-yl-carbamoyl]-methyl}Methyl-ditetradecyl-ammonium iodide: (8m)

In still another embodiment of the present invention, the compound of formula I is useful for useful for DNA ligase inhibition.

In yet another embodiment of the present invention, the compound of formula I are useful for the treatment of cancer, particularly for the treatment of breast cancer, liver cancer, prostate cancer.

In still another embodiment of the present invention, the compound of formula I show IC 50 values against various cancers cell lines is ranging between 1.8 µM to 20 µM.

In yet another embodiment of the present invention, the compound of formula I show IC50 value in the range of 1.872 to 8.748 µM for the inhibition of HepG2, NH/3T3, PC-3, MCF-7 cell lines.

In still another embodiment of the present invention, a process for the preparation of compounds of formula I, comprises the steps of:

(a) Boc protection of free amine group of amino acid L-Glutamine to obtain compound 1 followed by cyclization of (Boc)-Glutamine using DCC, NHS to generate glutarimide, a compound of formula 2;

(b) arylation of imide N—H group of glutarimide, the compound of formula obtained in step (a) using phenacyl bromide in the presence of a base $K_2CO_3$, at a temperature ranging from 25° C. to 80° C. for a period ranging from 8 to 12 hrs to obtain compound 3, followed by Boc deprotection to obtain amine intermediate compound 4;

(c) reacting compound 4 obtained from step (b) with Boc-glycine to produce the subsequent Boc glycine glutarimide intermediate compound 5;

(d) deprotecting compound 5 obtained from step (c) to obtain glycine conjugated free amine compound 6;

(e) reacting compound 6 obtained from step (d) with an alkyl bromide to form a compound of formula 7 followed by quaternization of the compound of formula 7 with an alkyl halide to obtain a compound of formula I.

In yet another embodiment of the present invention, the alkyl bromide used in a process for the preparation of compounds of formula 1, is having aliphatic hydrocarbon chain length selected from 2-22 carbon atoms.

In still another embodiment of the present invention, the alkyl halide used for quaternization is aliphatic hydrocarbon chain length selected from 1-5 carbon atoms.

In yet another embodiment of the present invention, the quaternization of the compound 7 obtained from step (e) of a process for the preparation of compounds of formula 1, is carried out at a temperature in the range of 10° C. to 40° C.

In still another embodiment of the present invention, the pharmaceutical composition comprises compound of formula 1 along with pharmaceutically acceptable additive and carriers.

The invention embodiments also include investigated in vitro anticancer potential of cationic lipidated cordiarimide molecules of formula I, in different cancer cell lines and evaluated effects of the proposed molecules on various biochemical pathways of cancer cell lines including the induction of apoptosis by phosphatidyl serine externalization, cell cycle arrest using flow cytometry and activation of caspase-3 activity.

BRIEF DESCRIPTION OF THE DRAWINGS

Scheme 1: Outlines the synthetic strategy employed for the preparing the proposed cationic lipid-cordiarimide hybrids described in the present invention.

ABBREVIATIONS

FACS: Fluorescent activated cell sorting
PI: Propidium iodide
BOC: di-tert-butyl-pyrocarbonate
TFA: Trifluoroacetic acid
MTT: 3-(4,5-dimethylthiazol-2-yl)-2,5-diphenyltetrazolium bromide
DMEM: Dulbecco's Modified Eagles Medium
RPMI: Roswell Park Memorial Institute medium
FBS: Fetal Bovine Serum
DCC: Dicyclohexyl carbodiimide
hLigI: Human ligase I
NHS: N Hydroxy Succinimide
DMF: Dimethylformamide
EDCL: 1-Ethyl-3-(3-dimethylaminopropyl)carbodiimide
HOBT: Hydroxybenzotriazole
FAM: Fluorescein Amidite
EMSA: Electrophoretic mobility shift assay

DETAILED DESCRIPTION OF THE INVENTION

The present invention provides cationic lipid-cordiarimide hybrid compounds of formula I and a process of the preparation thereof. The present invention also relates to the evaluation of their anticancer activity in various human cancer and non cancer cell lines. The novel cationic lipid based compounds containing cordiarimide moiety acts as anticancer drugs and specifically C12 analogue (8k) inhibits DNA ligation and kills cancer cells selectively with IC50 1.8 μM. The area of science that is likely to be benefited most from the present invention is targeted cancer therapy and in vitro and in vivo studies of DNA replication and repair. According to the practice of the present invention, "cationic" means the positive charge either on quaternized nitrogen or on a protonated nitrogen atom. The distinctive novel structural features common to the cationic lipidated cordiarimide disclosed in the present invention include: (1) The presence of hydrophobic groups which are directly linked to the positively charged nitrogen atom and (2) the presence of phenacylated glutarimide. As such, the disclosed cationic lipid hybrids may be represented by the following formula I.

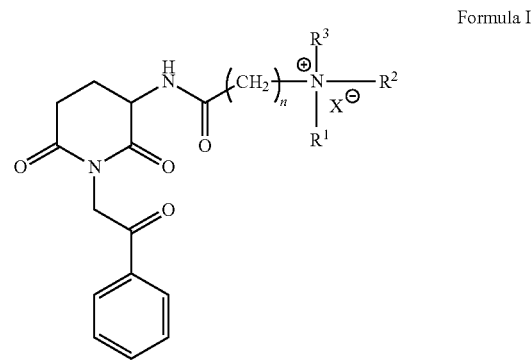

Figure 2A:
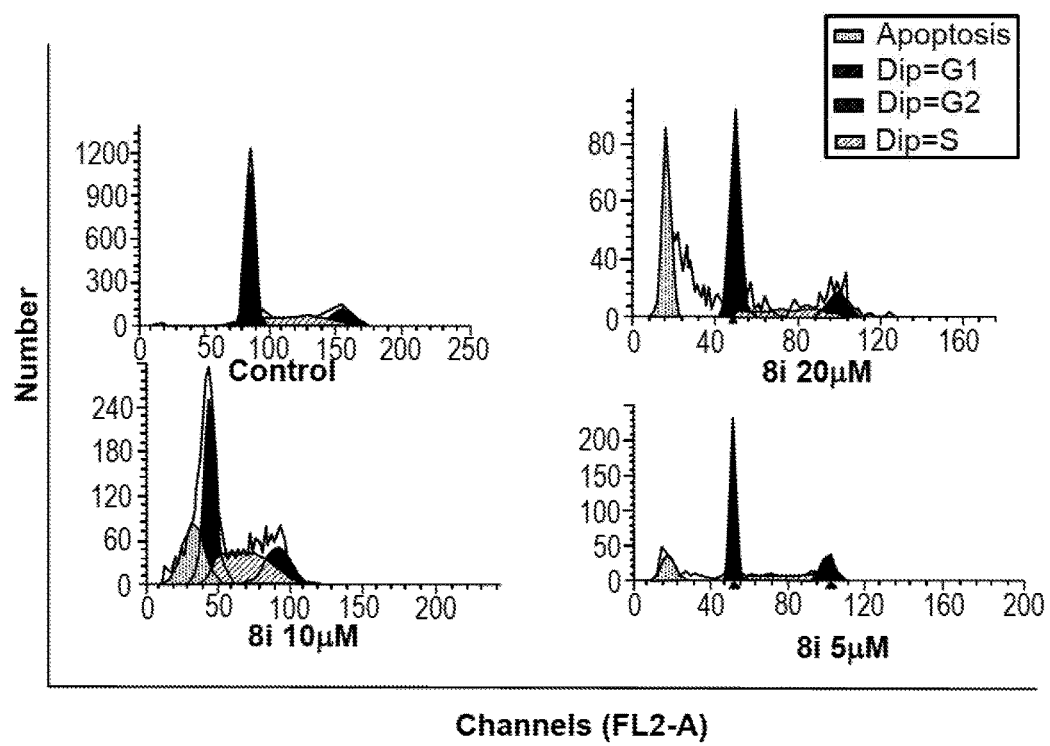
FIGS. 2A & 2B: illustrates cell cycle profiles of cationic lipid-cordiarimide hybrid 8i & 8k (0 mM, 5 mM, 10 mM, 20 mM) treated HepG2 cells. Cellular DNA was stained with 50 mg/mL PI in PBS. Stained cells were analyzed by FACScan flow cytometer (Becton Dickinson, USA). All the experiments were performed at least three times. Untreated cells (blank) were used as control. Data are expressed as % of cell count in each phase of cell cycle induced by compounds 8i & 8k in each concentration.
Figure 2A:
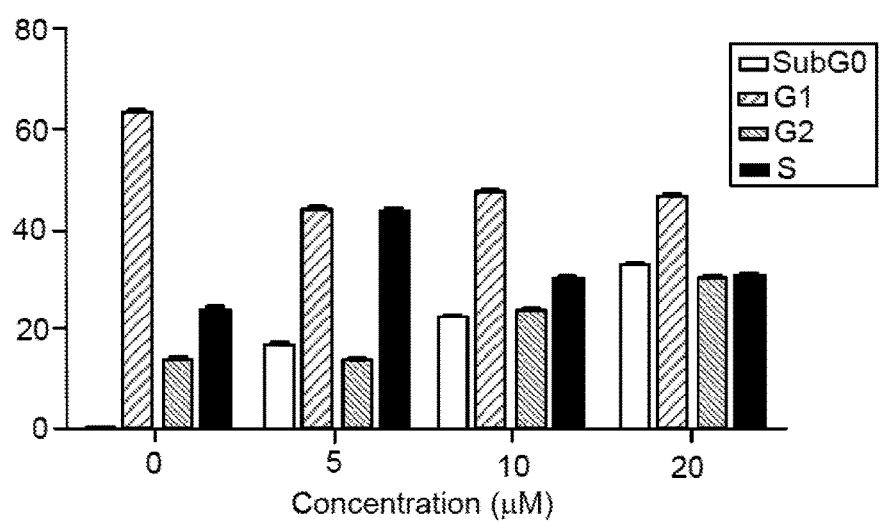
Figure 2B:
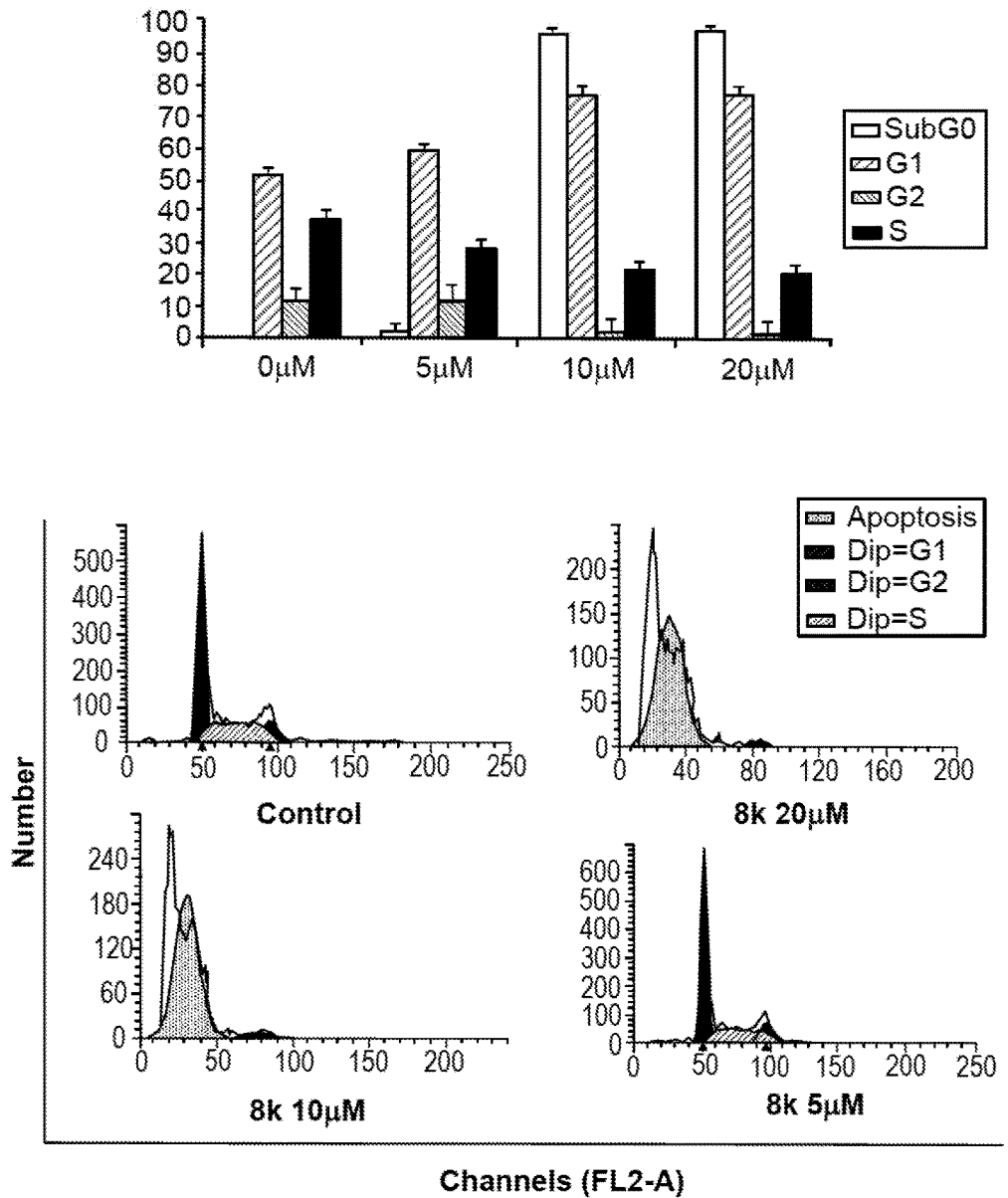
Figure 8:
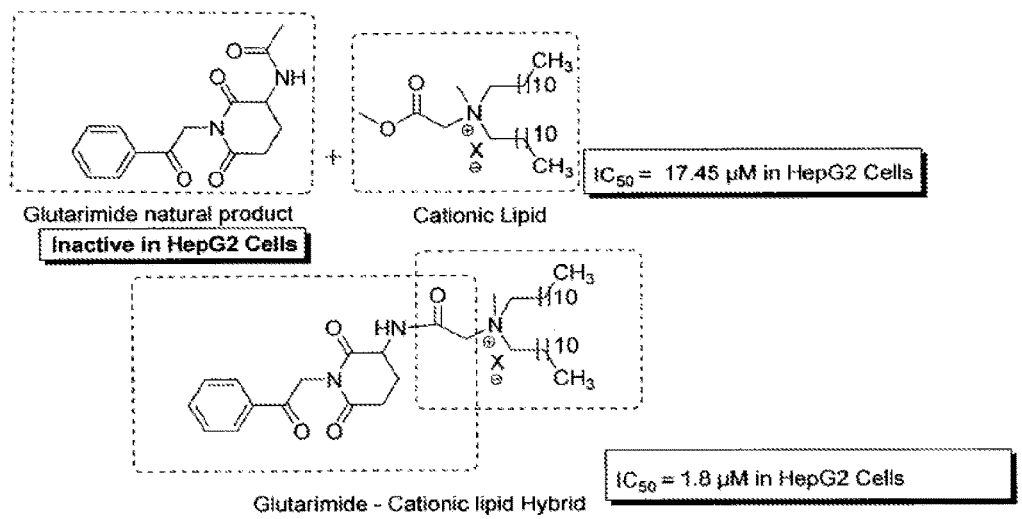
FIG. 8: Explain the anti cancer activities of parent molecules and the hybrid molecules. This scheme indicates that the lipid conjugation endowed phenomenal anticancer activity to inactive cordiarimide A.
Figure 9:
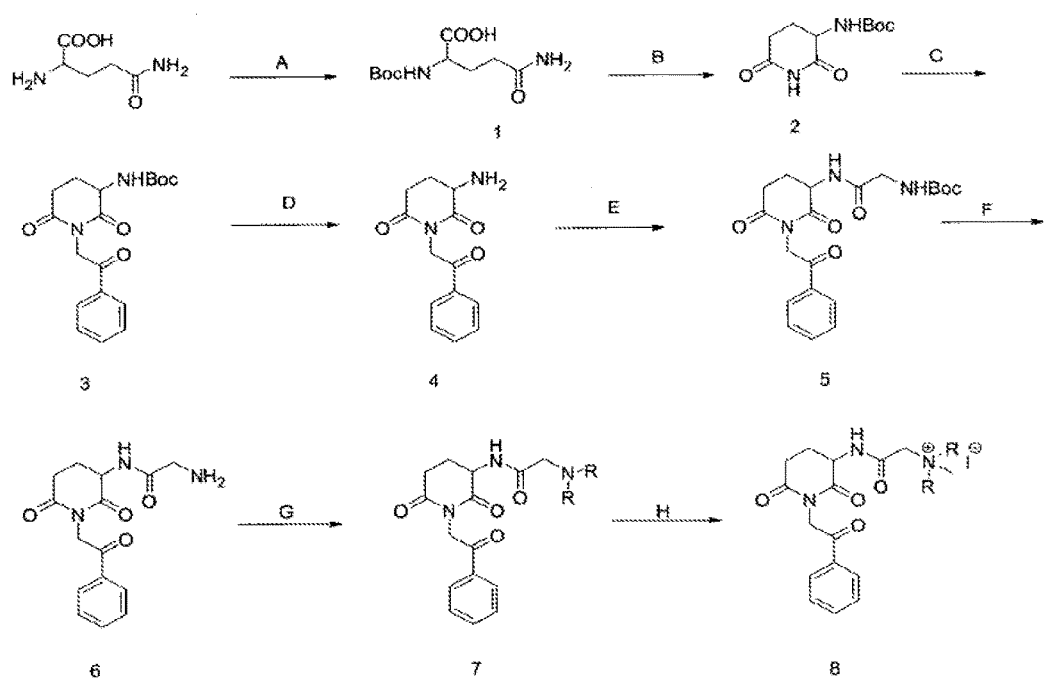
FIG. 9: Outline of the synthetic strategy employed for the preparing the proposed cationic lipid-cordiarimide hybrids described in the present invention.

Formula I

Wherein each of R1 and R2 is independently hydrogen or a lipophilic moiety containing at least two carbon atoms and is optionally selected from 2-22 carbon containing alkyl, mono-, di- and tri-unsaturated alkenyl (C2-C22) provided both R1 and R2 are not hydrogen; R3 is independently hydrogen or alkyl (C1-C5, straight or branched); n is an integer between 1 and 7 and X is optionally selected from chlorine, bromine or iodine atom. The structure and general synthesis adopted for preparing cationic cordiarimide compounds are outlined in scheme 1. As shown in scheme 1 the synthesis of cationic lipid cordiarimide hybrid compounds was achieved starting from the naturally occurring amino acid L-Glutamine (Procured from Spectrochem chemicals). In the first step the free amine of glutamine was protected with Boc anhydride and the resultant N (Boc)-Glutamine (compound 1) was cyclized in the second step using DCC, NHS to generate cyclic imide (compound 2). This was reacted with phenacyl bromide in the presence of $K_2CO_3$, acetonitrile at a temperature in the range of 25° C. to 80° C. for a period ranging between 8 to 12 hrs to generate intermediate (compound 3). The compound 3 was treated with TFA to deprotect the Boc and the resultant primary amine (compound 4) was reacted with Boc-Glycine to produce the intermediate compound 5. This intermediate was acidified to deprotect the Boc group and the resultant free amine (6) was alkylated with respective alkyl bromides using $K_2CO_3$ in EtOAc to get the twine chain tertiary amine intermediates 7a-7m. Subsequent quaternization of tertiary amine with methyl iodide at a temperature in the range of 10° C. to 40° C. to produce the proposed final compounds of formula I comprising the compounds 8a-8m. In the present proposal we have described the synthesis and biological evaluation of 13 different cationic lipidated cordiarimide compounds with varying alkyl chains starting from C2-C14. In the present invention we also included the screening data of 13 tertiary amine intermediates. Among these intermediates 7e-7g (table 1) are moderately active and cationic cordiarimide compounds 8f-8k (table 1) exhibited potential antiproliferative activity towards cancer cell lines. Further, we have analyzed the apoptosis induction potential disclosed active compounds of 8h-8k in HepG2 cells (FIG. 2). Apoptosis is one of the major cell death pathways induced by anticancer agents and we have evaluated apoptosis inducing effects of 8h-8k by Annexin V/Propidium iodide (PI) binding. The compound 8i and 8k induced significant amount of apoptosis (FIGS. 2a and 2b). Based on this data, we also examined the effect of 8i and 8k on the cell cycle of HepG2 cells by flow cytometry in PI (propidium iodide) stained cells after treatment with 8i and 8k or 24 h. FIGS. 2A & B shows the DNA distribution histograms of HepG2 cells in the absence (control) and presence (5, 10, and 20 mM) of compounds 8i and 8k respectively. From FIGS. 2 A & B it is evident that 8i did not show any impact on cell cycle progression but 8k blocked the cell cycle in G0/G1 phase. Both the compounds activated the casepase-3 in HepG2 cells dose dependently (FIG. 3) and this confirms that the apoptosis induction is due to caspase-3 activation by compounds 8i and 8k in HepG2 cells. These unique structural features of the disclosed cationic lipidated glutarimides may be responsible for the unusual anticancer activities, specifically DNA ligase I mediated anticancer activities of the novel cationic lipid 8k. In the present invention it is worth mentioning that longer alkyl chain (n>12) or short alkyl chain (n<6) have no activity at all while medium alkyl chain (n from 7 to 12) has significant activity against most of the tested cancer cell lines. The improved activity is highly dependent on the head group moiety and that too is highly chain length specific. Not all the combinations of head group moiety and carbon chain length produces anticancer property. There needs to be a specific combination in order to generate potential anticancer agents. In the present invention, the proposed cordiarimide has excellent compatibility with cationic lipid having chain length of 8 to 12 carbon and not others. Based on the mentioned examples, one cannot simply generalize that cationic lipid moiety enhances the activity of all small molecules. According to Kittakoop et al. cordiarimide A showed very weak cytotoxicity against only one cell line i.e. MOLT-3, exhibiting IC50 value of 145.3 μM, and it is inactive toward HepG2, A549, and HuCCA-1 cell lines. Whereas the hybrid compounds of the present invention demonstrated significantly high anticancer activity and especially 8k has shown very good selective anticancer activity in cancer cell lines PC-3, HepG2 and MCF-7 cells with IC-50 values 5.6, 1.8, 22.8 μM, respectively. This indicates that lipid conjugation endowed phenomenal anticancer activity to inactive cordiarimide A (FIG. 8).

Figure 4:
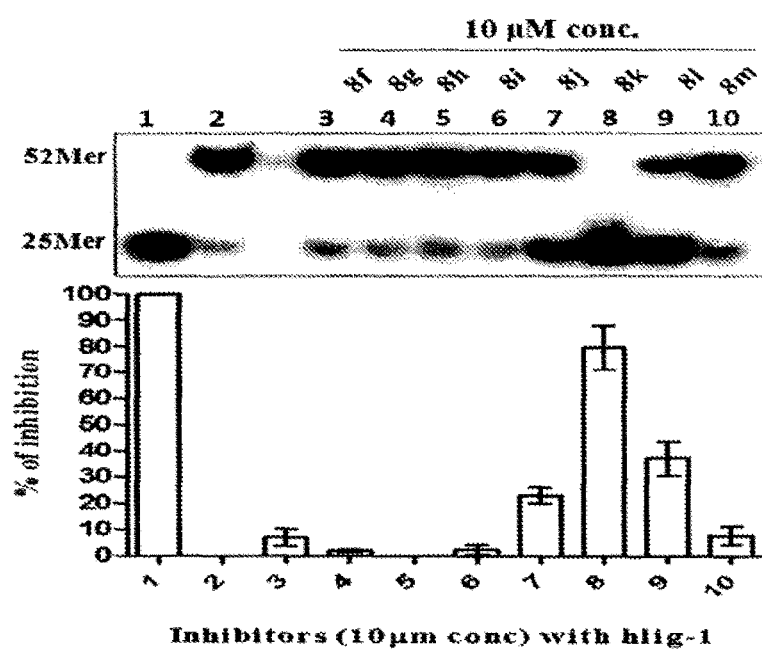
FIG. 4: Screening of 8f-8m for inhibition of ligation activity. 8k (lane 8) showed the complete inhibition of ligase I activity at 10 μM concentration.
Figure 5A:
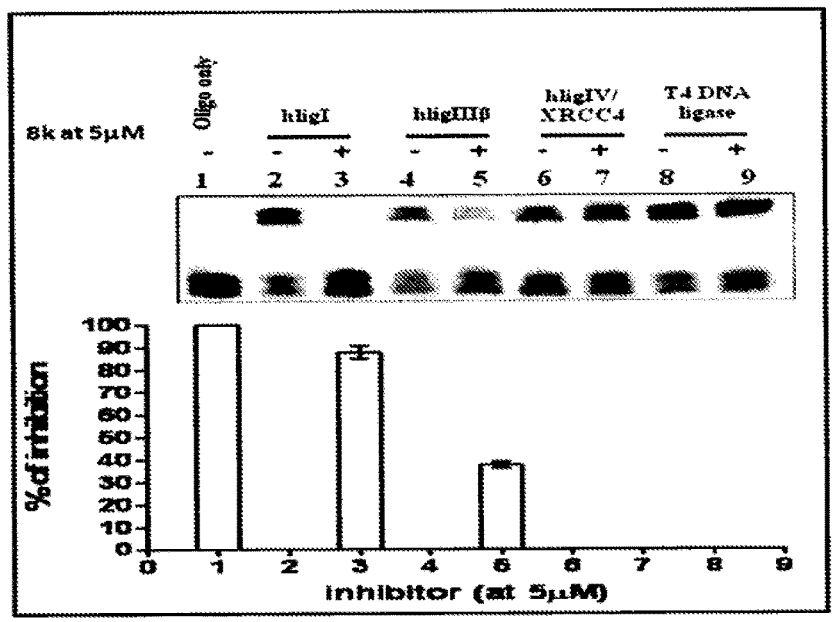
FIG. 5A: Selective inhibition of DNA ligase I activity is shown here. In lane 3 almost complete inhibition of ligase I activity is seen. In lane 5, partial inhibition of ligase IIIβ activity is seen. Lanes 7 and 9 show no inhibition of ligase IV and T4 DNA ligase activity respectively.
Figure 5B:
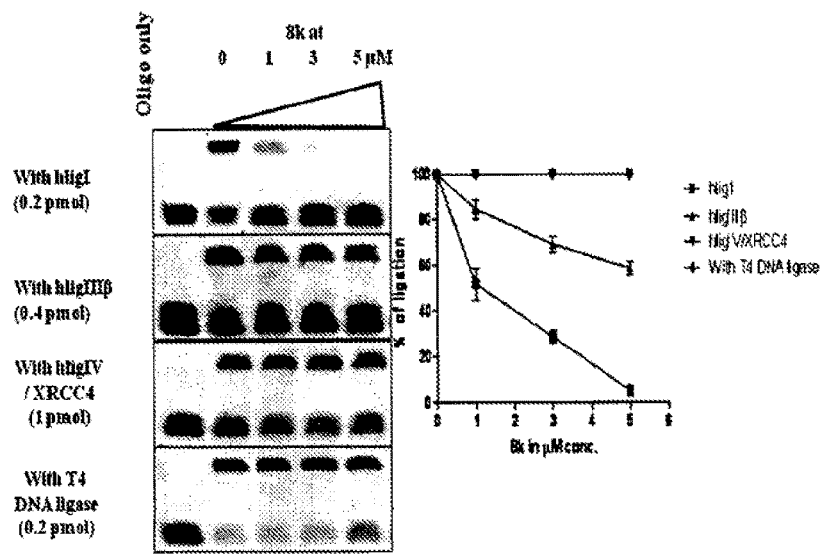
FIG. 5B: Concentration dependent activity of 8k is shown here with three different human ligases and T4 DNA ligase as control. Almost 50% inhibition of human ligase I activity is seen at 1 μM concentration whereas less than 50% inhibition of ligase IIIβ is seen even at 5 μM concentration. No appreciable inhibition of ligase IV or T4 ligase is observed at 5 μM concentration of 8k.

From $IC_{50}$ (table 1) data it is evident that the medium alkyl chain compounds 8f-8j exhibited non-specific antiproliferative activity. But 8k showed selective anti-proliferative activity at lower concentrations, especially in metastatic cell line (PC-3). In order to find out the reason why 8k has unique activity over other medium alkyl chain compounds, we have screened this molecule against some important proteins that are implicated in cancer cell evolution. Surprisingly 8k showed inhibition of DNA ligation (FIG. 4, FIGS. 5A & B). Human DNA ligases are fundamental proteins for DNA replication, recombination, and repair. They catalyze the formation of phosphodiester bonds between adjacent 5'-phosphoryl and 3'-hydroxyl termini at single strand breaks in duplex DNA molecules. Among the three forms of human ligases, hLigI is the major form in replicating cells and its level has been found to be elevated in some cancer cells. The potential of DNA ligases as targets for anti-cancer therapy has now been realized. Above data clearly demonstrates the possible reason for the selective anti-proliferative activity of 8k and this by inhibiting the DNA ligation in cancer cells.

TABLE 1

Summarizes the IC50 values of cationic lipid-cordiarimide hybrids (8a-8m) and respective tertiary amine intermediates (7a-7m) in μM against various cell lines.

| Compound (IC50 μM) | $R_3$ | $R_1$ & $R_2$ | PC-3 | HepG2 | MCF-7 | NIH/3T3 |
|---|---|---|---|---|---|---|
| 7a | H | $C_2H_5$ | >20 | >20 | >20 | >20 |
| 7b | H | $C_3H_7$ | >20 | >20 | >20 | >20 |
| 7c | H | $C_4H_9$ | >20 | >20 | >20 | >20 |
| 7d | H | $C_5H_{11}$ | >20 | 12.52 | >20 | >20 |
| 7e | H | $C_6H_{12}$ | >20 | 5.698 | 3.855 | 3.736 |
| 7f | H | $C_7H_{15}$ | >20 | 7.808 | 9.334 | 8.735 |
| 7g | H | $C_8H_{17}$ | >20 | 11.55 | 10.33 | 7.178 |
| 7h | H | $C_9H_{19}$ | >20 | >20 | 19.88 | 10.67 |
| 7i | H | $C_{10}H_{21}$ | >20 | >20 | 14.21 | >20 |
| 7j | H | $C_{11}H_{23}$ | 17.45 | >20 | >20 | >20 |
| 7k | H | $C_{12}H_{25}$ | >20 | >20 | >20 | >20 |
| 7l | H | $C_{13}H_{27}$ | >20 | >20 | >20 | >20 |
| 7m | H | $C_{14}H_{29}$ | >20 | >20 | >20 | >20 |
| 8a | $CH_3$ | $C_2H_5$ | >20 | >20 | >20 | >20 |
| 8b | $CH_3$ | $C_3H_7$ | >20 | >20 | >20 | >20 |
| 8c | $CH_3$ | $C_4H_9$ | >20 | >20 | >20 | >20 |
| 8d | $CH_3$ | $C_5H_{11}$ | >20 | >20 | >20 | >20 |
| 8e | $CH_3$ | $C_6H_{12}$ | >20 | >20 | >20 | >20 |
| 8f | $CH_3$ | $C_7H_{15}$ | >20 | 3.296 | >20 | >20 |
| 8g | $CH_3$ | $C_8H_{17}$ | >20 | 3.427 | 6.365 | 5.483 |

TABLE 1-continued

Summarizes the IC50 values of cationic lipid-cordiarimide hybrids (8a-8m) and respective tertiary amine intermediates (7a-7m) in μM against various cell lines.

| Compound (IC50 μM) | $R_3$ | $R_1$ & $R_2$ | PC-3 | HepG2 | MCF-7 | NIH/3T3 |
|---|---|---|---|---|---|---|
| 8h | $CH_3$ | $C_9H_{19}$ | 8.748 | 3.257 | 6.448 | 2.736 |
| 8i | $CH_3$ | $C_{10}H_{21}$ | 4.23 | 3.072 | 5.206 | 2.134 |
| 8j | $CH_3$ | $C_{11}H_{23}$ | >20 | 3.395 | 8.516 | 3.331 |
| 8k | $CH_3$ | $C_{12}H_{25}$ | 5.61 | 1.872 | >20 | >20 |
| 8l | $CH_3$ | $C_{13}H_{27}$ | >20 | >20 | >20 | >20 |
| 8m | $CH_3$ | $C_{14}H_{29}$ | >20 | >20 | >20 | >20 |

EXAMPLES

Following examples are given by way of illustrating the present invention and should not be construed to limit the scope of the present invention.

The detailed reaction conditions for the synthesis of cationic lipid-cordiarimide hybrid are illustrated in Scheme 1.

Example 1: N (Boc)-L-Glutamine (1)

L-Glutamine (25 g, 0.171 mol) (Procured from Spectrochem chemicals) was dissolved in (300 mL) of aqueous solution of NaOH (21.9, 0.547 mol). The solution was cooled and a solution of Boc anhydride (0.205) in THF (150 mL) was added at <10° C. (Exothermic reaction). Then the reaction mixture was stirred at 25° C. for 20 h. TLC control: MeOH, $CH_2Cl_2$ (1:1) with 0.1% AcOH. The organic phase was separated off, the water phase was extracted with hexane (100 mL), and acidified by 2N HCL to pH 2, and extracted with ethyl acetate (2×250 mL). Combined organic phase was dried over $Na_2SO_4$, then evaporated by vacuum, diluted with methylene chloride, and evaporated again. The product is obtained as a sticky oil, which could be crystallized by hexane to after standing for 2-3 days to yield N-(Boc)-L-glutamine (1) (37.5 g, 89%) as colorless solid.

$^1$H NMR (DMSO, 300 MHz) δ 7.27 (1H, s, OH), 6.97 (2H, d, J=7.92 Hz, NH), 3.83 (1H, m, J=4.29 Hz, H-3), 2.09 (2H, t, J=9.54 Hz, H-5), 1.9082-1.6856 (2H, m, H-4), 1.3687 (9H, s, H-6) ESI-MS (m/z): 269 (M+Na)$^+$

Example 2: Tert-Butyl (S)-2,6-dioxopiperidin-3-ylcarbamat (2)

To a solution of Boc-L-glutamine (Boc-L-Gly) (S) (1) (37 g, 0.150 mol), NHS (20.75 g, 0.180 mol) and DCC (30.9 mg, 0.150 mol) in dry EtoAc (700 mL) was added. The reaction mixture was stirred at 80° C. for 7 h. The resulting reaction mixture 1,3 dicyclohexyl-urea was formed as a by product. It was separated by filtration method and collected filtrate. The filtrate was washed with water (2×200 mL) followed by brine (150 mL). The organic phases were dried over $Na_2SO_4$, filtered and concentrated under reduced. The residue was purified by flash column chromatography on silica gel (60-120 mesh) (eluent: EtOAc/PE=1/1, volume ratio) to affords (24.66 g, 71% $R_f$ 0.5) as a white solid to obtain Tert-Butyl (S)-2,6-dioxopiperidin-3-ylcarbamat (2)

$^1$H NMR (CDCl3, 300 MHz) δ 8.27 (1H, s, NH), 4.31 (1H, t, J=5.73 Hz, H-6), 2.83-2.61 (2H, m, /H-5), 2.53 (1H, m, /H-5), 1.94-1.81 (1H, m, H5), 1.46 (9H, s, H-8) ESI-MS (m/z): 225.2 (M+H)$^+$

Example 3: 2,6-Dioxo-1-(2-oxo-2-phenyl-ethyl)-piperidine]-carbamic acid tert-butylester (3)

To a solution of ter-Butyl(s)-2,6-dioxopiperidine-3-ylcarbamat (2) (24.6 g, 108 mol) in dry Acetonitrile (300 mL) was added anhydrous $K_2CO_3$ (60.8 g, 0.434 mol) and 2 bromo1-phenyl-ethanone (62.2 g, 0.324 mol). The reaction mixture was stirred at temperature of 80° C. for 5 h. The reaction was monitored by TLC using EtOAc (5:5 v/v) as a solvent system, and then from the resulting reaction mixture separate off $K_2CO_3$ filtration method. The filtrate was evaporated under vacuum to afford the crude product. That was purified by column chromatography using 20% EtOAc-P.E as eluent to afford (14 g, 40%, $R_f$ 0.6 in EtOAc-P.E) pure compound of white solid of 2,6-Dioxo-1-(2-oxo-2-phenyl-ethyl)-piperidine]-carbamic acid tert butylester (3)

$^1$H NMR (CDCl$_3$, 300 MHz) δ 8.12 (1H, d, J=6.66 Hz, NH), 7.95 (2H, d, J=7.26 Hz, H-13/H-17), 7.61 (1H, t, J=7.95 Hz, H-15), 7.49 (2H, t, J=7.70 Hz, H-14/H-16), 5.21 (2H, d, J=5.73 Hz, H10), 4.45 (1H, t, J=6.60 Hz H-6), 2.98-2.75 (2H, m, H-4), 2.56-2.52 (1H, m, H-5eq), 2.09-1.96 (1H, m, H-5ax), 1.46 (8H, s, H-9H) ppm. ESI-MS (m/z): 346.3 (M+)$^+$ Example 4: 3-Amino-1-(2-oxo-2-phenyl-ethyl)-piperidine-2,6-dione (4)

To a solution of carbamic acid tert-butyl ester (3) (14 g, 0.048 mol) in dry DCM (75 mL) was slowly added trifluoro acetic acid (20.29 ml). The mixture was stirred at 25° C. for 30 min for 30 min and concentrated under reduced pressure to give a (8.48, 85% $R_f$ 0.4 in 10% MeOH/DCM) violet solid of compound (4)

$^1$H NMR (CDCl$_3$, 300 MHz) δ 7.94 (2H, d, J=7.47 Hz, H-13/H-17), 7.60 (1H, t, J=7.44 Hz, H-15), 7.48 (2H, t, J=7.26 Hz, H-14/H-16), 4.76 (2H, d, J=4.35, Hz, H10), 4.28-4.25 (1 m, H-6), 2.60-2.46 (2H, m, H-4), 2.38-2.26 (2H, m, 2) ppm. ESI-MS (m/z): 247.1 (M+H)$^+$ Example 5: {[2,6-Dioxo-1-(2-oxo-2-phenyl-ethyl)-piperidin-3-ylcarbamoyl]-methyl}-carbainic acid tert-butyl ester (5)

To a solution of 3-amino-1-(2-oxo-2-phenyl-ethyl-)-pipipridine-2,6-dione (4) (8.48 g 0.0344 mol) in dry DCM (70 ml) was added Boc glycine (7.224 g 0.0412), EDCL (7.46 g, 0.0378 mol), HOBT (1.39 g, 0.0102 mol), triethylamine (14 ml 0.206 mol) and the reaction mixture was stirred at 25° C. under nitrogen atmospire for 3 h. The reaction was monitored by TLC using (10% MeOH/DCM) as a solvent system the resulting reaction mixture washed with water (2×150 ml), followed by brine solution (120 ml). The organic phases were dried over Na2SO4, filtered and concentrated under reduced pressure. The residue was purified by flash column chromatography on silica gel (60-120 mesh) (eluent: MeOH-DCM=0.3% volume ratio) to affords pure compound (6.80, 48% $R_f$ 0.6 in 10% MeOH in DCM) of white solid of compound (5) $^1$H NMR (CDCl$_3$, 300 MHz) δ 7.96 (1H, d, J=7.23 Hz, NH), 7.96 (2H, d, J=7.23 Hz, H-13/H-17), 7.61 (1H, t, J=7.47 Hz, H-15), 7.49 (2H, t, J=7.53 Hz, H-14/H-16), 6.98 (1H, d, J=5.7 Hz, 5.21 (2H, d, J=9.90 Hz, H10), 4.76-4.69 (1H, m H-6), 3.88-3.84 (2H, m, H-9), 2.98-2.79 (2H, m, H-4), 2.57-2.54 (1H, m, H-5eq), 2.08-1.93 (1H, m, H-5ax), 1.46 (8H, s, H-9) ppm. ESI-MS (m/z): 403.1M+)$^+$ Example 6: 2-Amino-N-[2,6-dioxo-1-(2-oxo-2-phenyl-ethyl)-piperidin-3-yl]-acetamide (6)

To a solution of (5) (6.80 g, 0.0168 mol) in DCM (56 ml) was slowly added trifluoro acetic acid (8.4 ml, 0.084 mol).

The mixture was stirred at 25° C. for 30 min and concentrated under reduced pressure to give a (3.88 g, 75%, $R_f$ 0.3 in 10% MeOH in DCM) white solid of compound (6) $^1$H NMR (DMSO, 300 MHz) δ 8.95 (1H, d, J=8.76 Hz, NH), 8.15 (2H, s, H-18), 8.04, (2H, d, J=7.29 Hz, H-13/H-17), 7.71 (1H, t, J=7.35 Hz, H-15), 7.575 (2H, t, J=7.65 Hz, H-14/H-16), 5.17 (2H, s, H10), 4.93-4.85 (1H, m H-6), 3.64 (2H, s, H-9), 3.10-2.97 (1H, m, H-4)), 2.82-2.76 (1H, m, −4), 2.07-2.041 (2H, m, H-5H) ppm. ESI-MS (m/z): 304.1 (M+H).

Example 7: Representative Procedure for the Synthesis of Compound (7a-7m)

To solution of compound (6) (500 mg) in Dry EtOAc (25 mL), triethylamine (4 eq) various alkyl bromides (3 eq) ($C_nH_{2n+1}$Br, here n=2–14) were added. Reaction mixture was stirred at 80° C. temperature for 12 h. The reaction was monitored by TLC using EtOAc/PE6:4) as a solvent system, and then the resulting reaction mixture solvent was evaporated by reduced pressure and purified by flash column chromatography (elutent 30% EtOAc/P.E) to affords alkylated derivatives ($R_f$ 0.6 in 50% EtOAc-P.E).

Intermediate-1

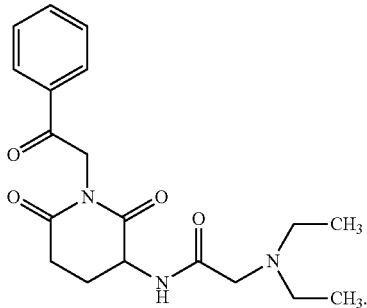 [SMILES: CCN(CC)CC(=O)NC1CCC(=O)N(CC(=O)c2ccccc2)C1=O]

2-Diethylamino-N-[2,6-dioxo-1-(2-oxo-2-phenyl-ethyl)-piperidin-3-yl]-acetamide: (7a)

Yellow oil, yield: 80.32%; $^1$H NMR (CDCl$_3$, 300 MHz) δ 8.15 (1H, d, J=5.37 Hz, NH), 7.95 (2H, d, J=7.20 Hz, H-13/H-17), 7.59 (1H, t, J=7.32 Hz, H-15), 7.49 (2H, t, J=7.71 Hz, H-14/H-16), 5.22 (2H, d, J=5.67 Hz, H10), 4.78-4.70 (1H, m, H-6), 3.08 (2H, d, H-9), 2.92-2.86 (2H, m, H-4), 2.60-2.54 (4H, m, H-a/H-a′), 2.09-1.94 (1H, m, H-5eq), 1.83 (1H, m, H-5ax), 1.03 (6H, t, J=7.11 Hz, H-d/H-d$^1$) ppm. ESI-MS (m/z): 360.3 (M+H)$^+$ Intermediate-2

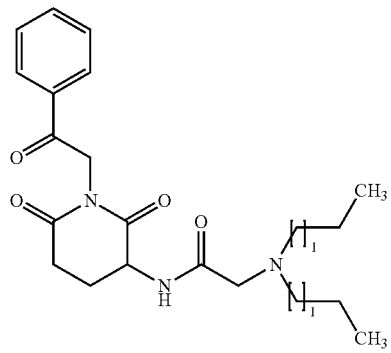

2-Dipropylamino-N-[2,6-dioxo-1-(2-oxo-2-phenyl-ethyl)-piperidin-3-yl]acetamide: (7b)

Yellow oil, yield: 75.6%; $^1$H NMR (CDCl$_3$, 300 MHz) δ 8.21 (1H, d, J=4.38 Hz, NH), 7.96 (2H, d, J=7.26 Hz, H-13/H-17), 7.61 (1H, t, J=7.14 Hz, H-15), 7.49 (2H, t, J=7.65 Hz, H-14/H-16), 5.22 (2H, d, J=4.14 Hz, H10), 4.78-4.70 (1H, m, H-6), 3.14 (2H, s, H-9), 2.99-2.87 (2H, m, H-4), 2.50 (4H, m, H-a/H-a′), 2.04-2.00 (1H, m, H-5eq), 1.65 (1H, m, H-5ax), 1.53-1.45 (4H, m, H-b/H-b$^1$), 1.25 (4H, m, H-c/H-c$^1$), 0.88 (6H, t, J=7.32 Hz, H-d/H-d$^1$) ppm. ESI-MS (m/z): 388.3 (M+H)$^+$ Intermediate-3

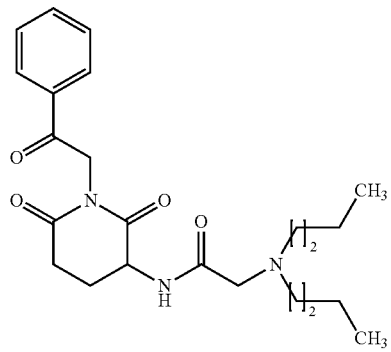

2-Dibutylamino-N-[2,6-dioxo-1-(2-oxo-2-phenyl-ethyl)-piperidin-3-yl]-acetamide: (7c)

Yellow oil, yield 72.2%; $^1$H NMR (CDCl$_3$, 300 MHz) δ 8.11 (1H, d, J=4.85 Hz, NH), 7.96 (2H, d, J=7.20 Hz, H-13/H-17), 7.61-7.59 (1H, m, H-15), 7.49 (2H, t, J=7.5 Hz, H-14/H-16), 5.3 (2H, d, J=4.8 Hz, H10), 4.78-4.72 (1H, m, H-6), 3.10 (2H, s, H-9), 2.93-2.82 (2H, m, H-4), 2.48 (4H, t, J=6.42 Hz, H-a/H-a$^1$), 2.09-1.94 (1H, m, H-5eq), 1.78 (1H, m, H-5ax), 1.43-1.41 (4H, m, H-b/H-b$^1$), 1.28-1.25 (4H, m, H-c/H-c$^1$), 0.88 (6H, t, J=7.2H-d/H-d$^1$) ppm. ESI-MS (m/z): 416.4 (M+H)$^+$

Intermediate-4

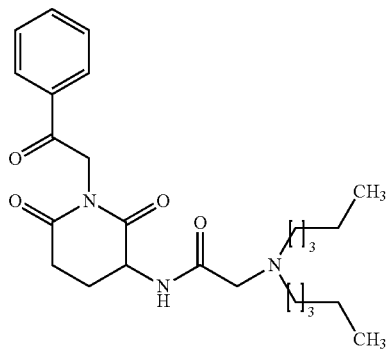

2-Dipentylamino-N-[2,6-dioxo-1-(2-oxo-2-phenyl-ethyl)-piperidin-3-yl]-acetamide: (7d)

Yellow oil, yield: 79.70%; $^1$H NMR (CDCl$_3$, 300 MHz) δ 8.12 (1H, d, J=5.70, NH), 7.96 (2H, d, J=7.38, H-13/H-17), 7.61-7.59 (1H, H-15), 7.49 (2H, t, J=7.38 Hz, H-14/H-16), 5.22 (2H, d, J=4.32 Hz, H10), 4.75-4.69 (1H, m, H-6), 3.10 (2H, s, H-9), 2.93-2.87 (2H, m, H-4), 2.47 (4H, t, J=7.02, Hz, H-a/H-a$^1$), 2.04-1.95 (2H, m, 2), 1.44-1.42 (4H, m, H-b/H-b$^1$), 1.25 (8H, m, H-c/H-c$^1$), 0.866 (6H, t, J=6.0, H-d/H-d$^1$) ppm. ESI-MS (m/z): 444.5 (M+H)$^+$

Intermediate-5

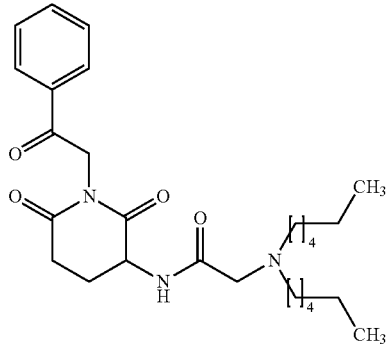

2-Dihexylamino-N-[2,6-dioxo-1-(2-oxo-2-phenyl-ethyl)-piperidin-3-yl]-acetamide: (7e)

Yellow oil, yield 72.51%; $^1$H NMR (CDCl$_3$, 300 MHz) δ 8.13 (1H, m, NH), 7.96 (2H, d, J=7.38 Hz, H-13/H-17), 7.61 (1H, t, J=6.75 Hz, H-15), 7.49 (2H, t, J=7.68 Hz, H-14/H-16), 5.22 (2H, d, J=3.72 Hz, H10), 4.77-4.69 (1H, m, H-6), 3.09 (2H, s, H-9), 2.99-2.87 (2H, m, 11-4), 2.47 (4H, t, J=6.15 Hz, H-a/H-a$^1$), 2.08-1.98 (1H, m, H-5eq), 1.63 (1H, m, H-5ax), 1.43-1.41 (4H, m, H-b/H-b$^1$), 1.25 (12H, m, H-c/H-c$^1$), 0.84-0.82 (6H, m, H-d/H-d$^1$) ppm. ESI-MS (m/z): 472.5 (M+H)$^+$

Intermediate-6

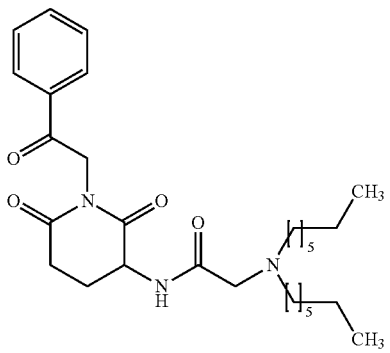

2-Diheptylamino-N-[2,6-dioxo-1-(2-oxo-2-phenyl-ethyl)-piperidin-3-yl]-acetamide: (7f)

Yellow oil, yield: 69.6%; $^1$H NMR (CDCl$_3$, 300 MHz) δ 8.11 (1H, d, J=6.65 Hz, NH), 7.96 (2H, d, J=7.26 Hz, H-13/H-17), 7.61 (1H, t, J=7.44 Hz, H-15), 7.49 (2H, t, J=7.68 Hz, H-14/H-16), 5.22 (2H, d, J=3.51 Hz, H10), 4.76-4.71 (1H, m, H-6), 3.09 (2H, s, H-9), 2.93-2.87 (2H, m, H-4), 2.47 (4H, t, J=6.15 Hz, H-a/H-a$^1$), 2.04-1.97 (1H, m, H-5eq), 1.59 (1H, m, H-5ax), 1.41 (4H, m, H-b/H-b$^1$), 1.25 (16H, m, H-c/H-c$^1$), 0.84 (6H, m, H-d/H-d$^1$) ppm. ESI-MS (m/z): 500.4 (M+H)$^+$

Intermediate-7

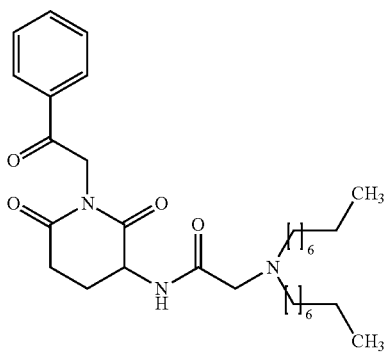

2-Dioctylamino-N-[2,6-dioxo-1-(2-oxo-2-phenyl-ethyl)-piperidin-3-yl]-acetamide: (7 g)

Yellow oil, yield: 74.52%; $^1$H NMR (CDCl$_3$, 300 MHz) δ 8.12 (1H, d, J=5.94 Hz, NH), 7.96 (2H, d, J=7.03 Hz, H-13/H-17), 7.61-7.5946 (1H, m, H-15), 7.52-7.49 (2H, m, H-14/H-16), 5.22 (2H, d, J=3.90 Hz, H10), 4.75-4.71 (1H, m, H-6), 3.09 (2H, s, H-9), 2.93-2.88 (2H, m, H-4), 2.46 (4H, m, H-a/H-a$^1$), 2.04-1.98 (1H, m, H-5eq), 1.66 (1H, m, H-5ax), 1.42 (4H, m, H-b/H-b$^1$), 1.25 (20H, m, H-c/H-c$^1$), 0.84 (6H, m, H-d/H-d$^1$) ppm. ESI-MS (m/z): 528.4 (M+H)$^+$

Intermediate-8

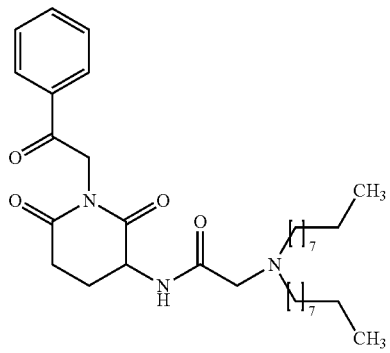

2Dinonylamino-N-[2,6-dioxo-1-(2-oxo-2-phenyl-ethyl)-piperidin-3-yl]-acetamide: (7h)

Yellow oil, yield: 79.47%; $^1$H NMR (CDCl$_3$, 300 MHz) δ 8.12 (1H, d, J=6.87 Hz, NH), 7.96 (2H, d, J=7.17 Hz, H-13/H-17), 7.62 (1H, t, J=7.47 Hz, H-15), 7.49 (2H, t, J=7.71 Hz, H-14/H-16), 5.22 (2H, d, J=4.23 Hz, H10), 4.78-4.69 (1H, m, H-6), 3.09 (2H, s, H-9), 2.99-2.81 (2H, m, H-4), 2.46 (4H, t, J=6.30 Hz, H-a/H-a$^l$), 2.04-1.98 (1H, m, H-5eq), 1.78 (1H, m, H-5ax), 1.41 (4H, m, H-b/H-b$^1$), 1.25-1.23 (24H, m, H-c/H-c$^1$), 0.86 (6H, t, J=4.17 Hz, H-d/H-d$^1$) ppm. ESI-MS (m/z): 556.5 (M+H)$^+$

Intermediate-9

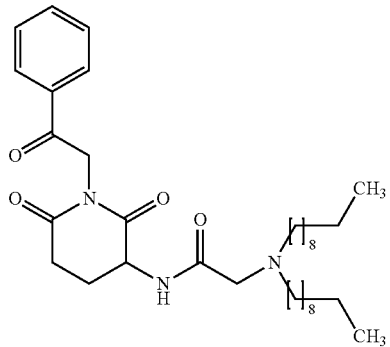

2-(Bis-decyl-amino)-N-[2,6-dioxo-1-(2-oxo-2-phenyl-ethyl)-piperidin-3-yl]acetamide: (7i)

Yellow oil, yield: 80.99%; $^1$H NMR (CDCl$_3$, 300 MHz) δ 8.11 (1H, d, J=5.13 Hz, NH), 7.96 (2H, d, J=7.5 Hz, H-13/H-17), 7.61 (1H, t, J=6.0 Hz, H-15), 7.49 (2H, t, J=7.5 Hz, H-14/H-16), 5.22 (2H, d, J=4.23 Hz, H10), 4.78-4.69 (1H, m, H-6), 3.09 (2H, s, H-9), 2.93-2.81 (2H, m, H-4), 2.46 (4H, t, J=6.30 Hz, H-a/H-a$^l$), 2.04-1.98 (1H, m, H-5eq), 1.78 (1H, m, H-5ax), 1.41 (4H, m, H-b/H-b$^1$), 1.24-1.22 (28H, m, H-c/H-c$^1$), 0.86 (6H, t, J=4.17 Hz, H-d/H-d$^l$) ppm. ESI-MS (m/z): 584.5 (M+H)$^+$

Intermediate-10

N-[2,6-Dioxo-1-(oxo-2-phenyl-ethyl)-piperidine-3-yl]-2-diundecylamino-acetamide (7j)

Yellow oil, yield: 70.40%; $^1$H NMR (CDCl$_3$, 300 MHz) δ 8.13 (1H, d, J=6.87 Hz, NH), 7.96 (2H, d, J=7.17 Hz, H-13/H-17), 7.61 (1H, t, J=7.47 Hz, H-15), 7.49 (2H, t, J=7.71 Hz, H-14/H-16), 5.22 (2H, d, J=4.23 Hz, H10), 4.78-4.69 (1H, m, H-6), 3.09 (2H, s, H-9), 2.93-2.87 (2H, m, H-4), 2.48 (4H, t, J=6.3 Hz, H-a/H-a$^1$), 2.04-1.98 (1H, m, H-5eq), 1.78 (1H, m, H-5ax), 1.41 (4H, m, H-b/H-b$^1$), 1.25-1.23 (32H, m, H-c/H-c$^1$), 0.86 (6H, t, J=4.17 Hz, H-d/H-d$^1$) ppm. ESI-MS (m/z): 612.5 (M+H)$^+$

Intermediate-11

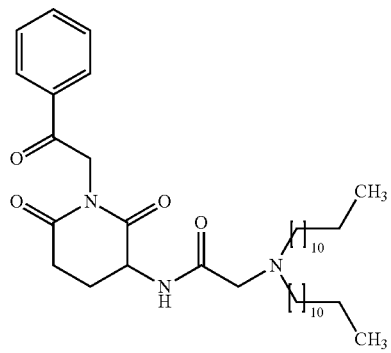

N-[2,6-Dioxo-1-(oxo-2-phenyl-ethyl)-piperidine-3-yl]-2-didodecylamino-acetamide: (7k)

Yellow oil, yield: 75.43%; $^1$H NMR (CDCl$_3$, 300 MHz) δ 8.13 (1H, d, J=7.50 Hz, NH), 7.96 (2H, d, J=7.20 Hz, H-13/H-17), 7.60 (1H, t, J=7.05 Hz, H-15), 7.496 (2H, t, J=7.59 Hz, H14/H-16), 5.22 (2H, d, J=4.65 Hz, H10), 4.76-4.71 (1H, m, H-6), 3.09 (2H, s, H-9), 2.93-2.87 (2H, m, H-4), 2.47-2.39 (4H, m, H-a/H-a$^1$), 2.04-1.98 (2H, m), 1.42 (4H, m, H-b/H-b$^1$), 1.25 (40H, m, H-c/H-c$^1$), 0.87-0.85 (6H, m, H-d/H-d$^1$) ppm. ESI-MS (m/z): 640.5 (M+H)$^+$ Intermediate-12

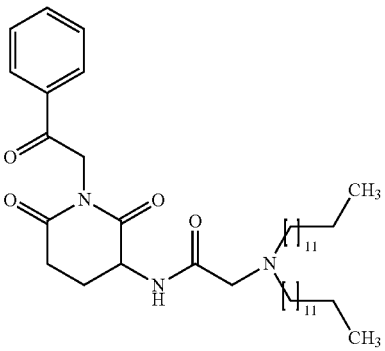

N-[2,6-Dioxo-1-(oxo-2-phenyl-ethyl)-piperidine-3-yl]-2-ditridecylamino-acetamide: (7ll)

Yellow oil, yield: 80.2%; $^1$H NMR (CDCl$_3$, 300 MHz) δ 8.12 (1H, d, J=6.64 Hz, NH), 7.96 (2H, d, J=7.21 Hz, H-13/H-17), 7.61 (1H, t, J=7.50 Hz, H-15), 7.48 (2H, t, J=7.67 Hz, H14/H-16), 5.22 (2H, d, J=4.26 Hz, H10), 4.77-4.69 (1H, m, H-6), 3.09 (2H, s, H-9), 2.93-2.87 (2H, m, H-4), 2.46 (4H, t, J=6.15 Hz, H-a/H-a$^1$), 2.04-1.97 (1H, m, H-5eq), 1.67 (1H, m, H-5ax), 1.42 (4H, m, H-b/H-b$^1$), 1.24-1.22 (40H, m, H-c/H-c$^1$), 0.87-0.85 (6H, m, H-d/H-d$^1$) ppm. ESI-MS (m/z): 668.5 (M+H)$^+$ Intermediate-13

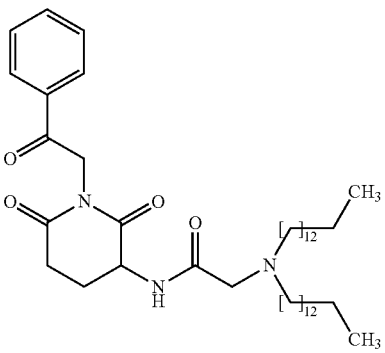

N-[2,6-Dioxo-1-(oxo-2-phenyl-ethyl)-piperidine-3-yl]-2-ditetradecylamino-acetamide 7m)

Yellow oil, yield: 60%; $^1$H NMR (CDCl$_3$, 300 MHz) δ 8.12 (1H, d, J=6.66 Hz, NH), 7.96 (2H, d, J=7.20 Hz, H-13/H-17), 7.61 (1H, t, J=7.50 Hz, H-15), 7.50 (2H, t, J=7.68 Hz, H-14/H-16), 5.22 (2H, d, J=4.26 Hz, H10), 4.77-4.69 (1H, m, H-6), 3.09 (2H, s, H-9), 2.93-2.87 (2H, m, H-4), 2.46 (4H, t, J=6.15 Hz, H-a/H-a$^1$), 2.04-1.97 (1H, m, H-5eq), 1.67 (1H, m, H-5ax), 1.42 (4H, m, Hb/H-b$^1$), 1.24-1.22 (44H, m, H-c/H-c$^1$), 0.87-0.85 (6H, m, H-d/H-d$^1$) ppm. ESI-MS (m/z): 696.6 (M+H)$^+$ Example 8: Representative Procedure for the Synthesis of Compound (8a-8m)

To solution of compound (7) (200 mg) in Dry DCM (5 ml) methyl iodide (10 eq) was added. Reaction mixture was stirred at 25° C. for 12 h. The reaction was monitored by TLC using 10% MeOH/DCM as a solvent system, and then the resulting reaction mixture solvent was evaporated by reduced pressure. The resulting crude was purified by flash column chromatography (elutent 3% MeOH/DCM) (R$_f$ 0.3 in 10% MeOH-DCM).

Compound 8(a)

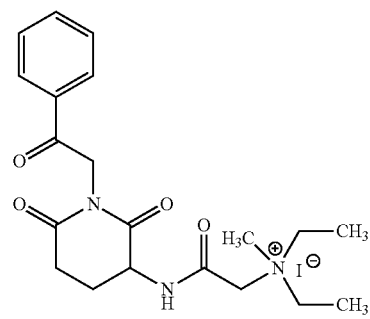 [SMILES: CC[N+](C)(CC)CC(=O)NC1CCC(=O)N(CC(=O)c2ccccc2)C1=O ; [I-]]

{[2,6-Dioxo-1-(2-oxo-2-phenyl-ethyl)-piperidin-3-ylcarbamoyl]-methyl}-Diethyl-methyl-ammonium iodide: (8a)

Yellow solid, yield: 60%; $^1$H NMR (CDCl$_3$, 300 MHz) δ 9.29 (1H, d, J=7.53 Hz, NH), 7.95 (2H, d, J=7.14 Hz, H-13/H-17), 7.59 (1H, J=7.32 Hz, H-15), 7.48 (2H, t, J=7.38 Hz, H-14/H-16), 5.19 (2H, s, H10), 4.86-4.79 (2H, m, H-9), 4.33 (1H, d, J=13.68 Hz, H-6), 3.67-3.65 (4H, m, H-a/H-a$^l$), 3.36 (3H, s, H-e) 2.96 (1H, m, H-4eq), 2.86-2.76 (1H, m, H-4ax), 2.61-2.49 (1H, m, H-5eq), 2.29-2.26 (1H, m, H-5ax), 1.43 (6H, t, J=6.84 Hz, H-d/H-d$^1$) ppm. ESI-MS (m/z): 374.4 (M+)$^+$ Compound 8(b)

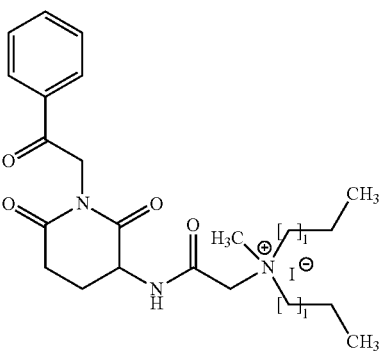

Dipropylamm{[2,6-Dioxo-1-(2-oxo-2-phenyl-ethyl)-piperidin-3-ylcarbamoyl]-methyl}-methyl-ammonium iodide: (8b)

Yellow oil, yield: 80%; $^1$H NMR (CDCl$_3$, 300 MHz) δ 9.37 (1H, d, J=7.89 Hz, NH), 7.95 (2H, d, J=7.26 Hz, H-13/H-17), 7.59 (1H, d, J=7.29 Hz, H-15), 7.48 (2H, t, J=7.83 Hz, H-14/H-16), 5.19 (2H, s, H10), 4.84-4.77 (2H, m, H-9), 4.33 (1H, d, J=13.53 Hz, H-6), 3.51-3.48 (4H, m, H-a/H-a¹), 3.38 (3H, s, H-e) 3.01-2.95 (1H, m, H-4eq), 2.88-2.76 (1H, m, H-4ax), 2.57-2.47 (1H, m, H-5eq), 2.27 (1H, m, H-5ax), 1.84-1.79 (4H, m, H-b/H-b¹), 1.03 (6H, t, J=7.17 Hz, H-d/H-d¹) ppm. ESI-MS (m/z): 402.32 (M+H)⁺

Compound 8(c)

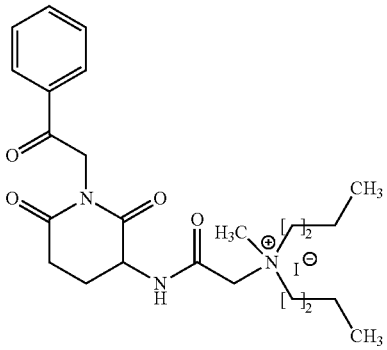

Dibutyl-{[2,6-dioxo-1-(2-oxo-2-phenyl-ethyl)-piperidin-3-ylcarbamoyl]-methyl}-methyl-ammonium iodide: (8c)

Yellow oil, yield: 75.3%; ¹H NMR (CDCl₃, 300 MHz) δ 9.30 (1H, d, J=8.11 Hz, NH), 7.95 (2H, d, J=8.19 Hz, H-13/H-17), 7.60 (1H, d, J=7.34 Hz, H-15), 7.49 (2H, t, J=7.63 Hz, H-14/H-16), 5.19 (2H, s, H10), 4.84-4.79 (2H, m, H-9), 4.33 (1H, d, J=13.76 Hz, H-6), 3.55-3.52 (4H, m, H-a/H-a¹), 3.37 (3H, s, H-e) 3.00-2.95 (1H, m, H-4eq), 2.87-2.75 (1H, m, H-4ax), 2.62-2.49 (1H, m, H-5eq), 2.28-2.25 (1H, m, H-5ax), 1.77-1.72 (4H, m, H-b/H-b¹), 1.45 (4H, q, J=7.41 Hz H-c/H-c¹), 0.99 (6H, t, J=7.28 Hz, H-d/H-d¹) ppm. ¹³C NMR (CDCl₃, 300 MHz) 191.5, 170.8, 170.0, 163.0, 134.7, 133.9, 128.9, 128.1, 128.0, 63.1, 63.0, 61.5, 50.8, 49.9, 31.5, 24.6, 22.7, 14.6, 13.6 ppm. ESI-MS (m/z): 430.3 (M+H)⁺

Compound 8(d)

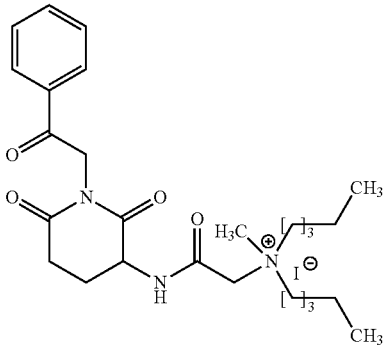

{[2,6-Dioxo-1-(2-oxo-2-phenyl-ethyl)-piperidin-3-ylcarbamoyl]-methyl}-Methyl-dipentyl-ammonium iodide: (8d)

Yellow oil, yield: 80.24%; ¹H NMR (CDCl₃, 300 MHz) δ 9.36 (1H, d, J=7.68 Hz, NH), 7.95 (2H, d, J=7.32 Hz, H-13/H-17), 7.60 (1H, d, J=7.25 Hz, H-15), 7.48 (2H, t, J=7.67 Hz, H-14/H-16), 5.19 (2H, s, H10), 4.82-4.77 (2H, m, H-9), 4.36 (1H, d, J=13.76 Hz, H-6), 3.54-3.505 (4H, m, H-a/H-a¹), 3.38 (3H, s, H-e) 2.99-2.95 (1H, m, H-4eq), 2.86-2.76 (1H, m, H-4ax), 2.59-2.48 (1H, m, H-5eq), 2.28-2.25 (1H, m, H-5ax), 1.78-1.76 (4H, m, H-b/H-b¹), 1.37-1.25 (8H, m, H-c/H-c¹), 0.90 (6H, t, J=6.74 Hz, H-d/H-d¹) ppm. ¹³C NMR (CDCl3, 300 MHz) 191.5, 170.8, 170.0, 163.0, 134.7, 133.9, 128.9, 128.1, 63.3, 63.2, 61.5, 50.8, 49.9, 46.6, 31.5, 28.2, 22.7, 22.4, 22.2, 13.8 ppm. ESI-MS (m/z): 458.3 (M+)⁺

Compound 8(e)

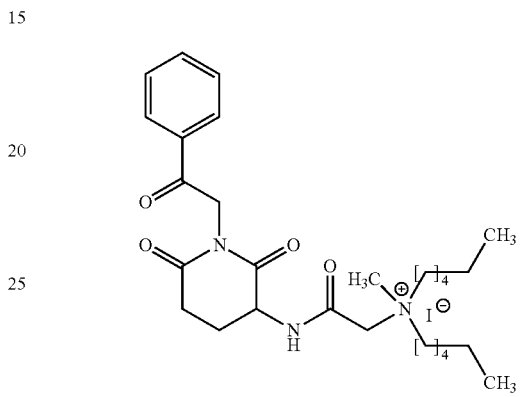

{[2,6-Dioxo-1-(2-oxo-2-phenyl-ethyl)-piperidin-3-ylcarbamoyl]-methyl}-Dihexyl-methyl-ammonium iodide: (8e)

Yellow oil, yield: 76.24.6%; ¹H NMR (CDCl3, 300 MHz) δ 9.32 (1H, d, J=7.71 Hz, NH), 7.95 (2H, d, J=7.55 Hz, H-13/H-17), 7.60 (1H, t, J=7.31 Hz, H-15), 7.48 (2H, t, J=7.74 Hz, H-14/H-16), 5.19 (2H, s, H10), 4.83-4.75 (2H, m, H-9), 4.35 (1H, d, J=13.78 H-6), 3.54-3.49 (4H, m, H-a/H-a¹), 3.29 (3H, s, H-e) 2.99-2.95 (1H, m, H-4eq), 2.86-2.77 (1H, m, H-4ax), 2.60-2.49 (1H, m, H-5eq), 2.29-2.25 (1H, m, H-5ax), 1.78-1.74 (4H, m, H-b/H-b¹), 1.33-1.25 (12H, m, H-c/H-c¹), 0.87 (6H, t, J=7.26 Hz H-d/H-d¹) ppm. ¹³C NMR (CDCl3, 300 MHz) 13.9, 22.4, 22.6, 25.9, 31.5, 46.5, 49.9, 50.8, 61.4, 63.2, 128.1, 128.9, 133.9, 134.7, 162.9, 169.9, 170.8, 191.4 ppm. ESI-MS (m/z): 486.4 (M+)⁺

Compound 8(f)

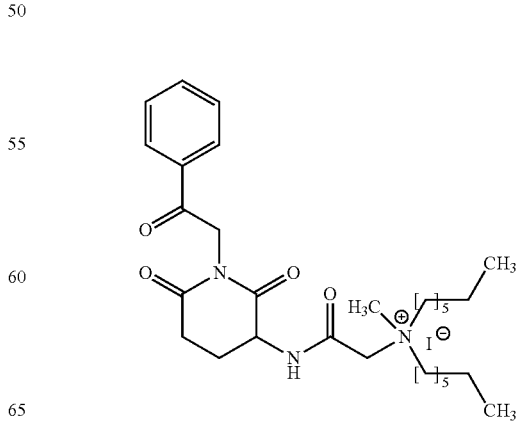

{[2,6-Dioxo-1-(2-oxo-2-phenyl-ethyl)-piperidin-3-ylcarbamoyl]-methyl}-Diheptyl-methyl-ammonium iodide: (8f)

Yellow oil, yield: 75.6%; ¹H NMR (CDCl₃, 300 MHz) δ 9.35 (1H, d, J=7.86 Hz, NH), 7.96 (2H, d, J=7.71 Hz, H-13/H-17), 7.60 (1H, t, J=6.90 Hz, H-15), 7.48 (2H, t, J=7.53 Hz, H-14/H-16), 5.19 (2H, s, H10), 4.85-4.75 (2H, m, H-9), 4.32 (1H, d, J=13.63 Hz, H-6), 3.52 (4H, m, H-a/H-a¹), 3.37 (3H, s, H-e) 3.00-2.95 (1H, m, H-4eq), 2.85-2.77 m, H-4ax), 2.61-2.50 (1H, m, H-5eq), 2.28-2.26 (1H, m, H-5ax), 1.75-1.74 (4H, m, H-b/H-b¹), 1.35-1.25 (24H, m, H-c/H-c¹), 0.86 (6H, t, J=6.75) ppm. ¹³C NMR (CDCl₃, 300 MHz) 14.0, 22.4, 22.7, 26.2, 28.7, 31.5, 46.6, 49.9, 50.8, 61.5, 63.2, 63.3, 128.1, 128.9, 133.81, 134.89, 162.9, 169.9, 170.8, 191.4 ppm. ESI-MS (m/z): 514.4 (M+)⁺

Compound 8(g)

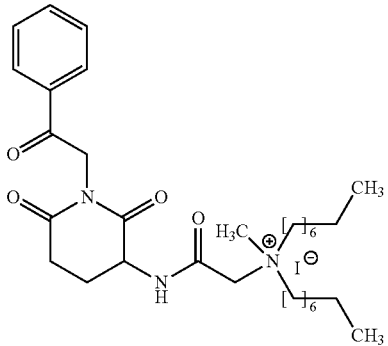

{[2,6-Dioxo-1-(2-oxo-2-phenyl-ethyl)-piperidin-3-ylcarbamoyl]-methyl}-Methyl-dioctyl-ammonium iodide: (8g)

Yellow oil, yield: 72.4%); ¹H NMR (CDCl₃, 300 MHz) δ 9.35 (1H, d, J=7.95 Hz, NH), 7.95 (1H, d, J=7.48 Hz, H-15), 7.60 (2H, t, J=7.96 Hz, H-14/H-16), 7.48 (2H, t, J=7.86 Hz, H-14/H-16) 5.19 (2H, s, H10), 4.84-4.76 (2H, m, H-9), 4.32 (1H, d, J=13.66 Hz, H-6), 3.53-3.49 (4H, m, H-a/H-a¹), 3.37 (3H, s, H-e) 3.00-2.96 (1H, m, H-4eq), 2.86-2.77 (1H, m, H-4ax), 2.60-2.49 (1H, m, H-5eq), 2.29-2.27 (1H, m, H-5ax), 1.69 (4H, m, H-b/H-b¹), 1.35-1.25 (24H, m, H-c/H-c¹), 0.86 (6H, t, J=6.94 /H-d¹) ppm. ¹³C NMR (CDCl₃, 300 MHz) 14.0, 22.5, 22.6, 26.1, 28.9, 31.4, 31.5, 46.5, 459.8, 50.7, 61.4, 63.1, 128.0, 128.8, 133.8, 169.9, 170.7, 191.8 ppm. ESI-MS (m/z): 542.4 (M+)⁺

Compound 8(h)

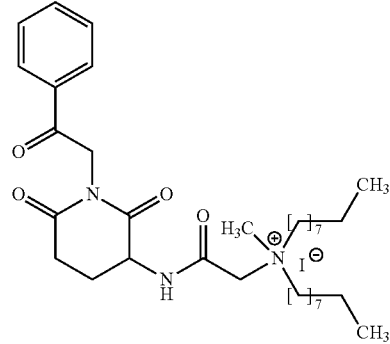

{[2,6-Dioxo-1-(2-oxo-2-phenyl-ethyl)-piperidin-3-ylcarbamoyl]-methyl}-Methyl-dinonyl-ammonium iodide: (8h)

Yellow oil, yield: 65.5%; ¹H NMR (CDCl₃, 300 MHz) δ 9.38 (1H, d, J=7.61 Hz, NH), 7.96 (2H, d, J=7.29 Hz, H-13/H-17), 7.60 (1H, t, J=7.22 Hz, H-15), 7.48 (2H, t, J=7.64 Hz, H-14/H-16), 5.19 (2H, s, H10), 4.85-4.75 (2H, m, H-9), 4.32 (1H, d, J=13.51 Hz, H-6), 3.52-3.50 (4H, m, H-a/H-a¹), 3.37 (3H, s, H-e) 3.00-2.99 (1H, m, H-4eq), 2.86-2.77 (1H, m, H-4ax), 2.60-2.49 (1H, m, H-5eq), 2.29-2.25 (1H, m, H-5ax), 1.74-1.70 (4H, m, H-b/H-b¹), 1.35-1.25 (24H, m, H-c/H-c¹), 0.87 (6H, t, J=6.40 H-d/H-d¹) ppm. ¹³C NMR (CDCl₃, 300 MHz) 14.1, 22.6, 26.2, 29.1, 29.1, 29.3, 29.7, 31.5, 31.8, 46.6, 49.9, 50.8, 61.5, 63.1, 128.1, 128.9, 133.9, 134.7, 162.9, 169.9, 170.8, 191.4 ppm. ESI-MS (m/z): 570.5 (M+)⁺

Compound 8(i)

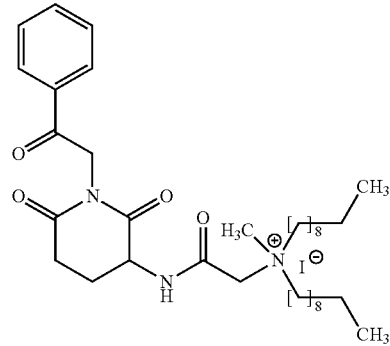

Bis-decyl-{[2,6-dioxo-1-(2-oxo-2-phenyl-ethyl)-piperidin-3-ylcarbamoyl]-methyl}-methyl-ammonium iodide: (8i)

Yellow oil, yield: 66.032%; ¹H NMR (CDCl₃, 300 MHz) δ 9.39 (1H, d, J=8.26 Hz, NH), 7.96 (2H, d, J=7.72 Hz, H-13/H-17), 7.60 (1H, t, J=7.37 Hz, H-15), 7.48 (2H, t, J=7.69 Hz, H-14/H-16), 5.19 (2H, s, H10), 4.86-4.79 (2H, m, H-9), 4.29 (1H, d, J=13.36 Hz, H-6), 3.51-3.49 (4H, m, H-a/H-a¹), 3.37 (3H, s, H-e) 3.00-2.96 (1H, m, H-4eq), 2.86-2.77 (1H, m, H-4ax), 2.60-2.519 (1H, m, H-5eq), 2.30-2.25 (1H, m, H-5ax), 1.74-1.67 (4H, m, H-b/H-b$^1$), 1.35-1.25 (28H, m, H-c/H-c$^1$), 0.87. (6H, t, J=7.03 Hz, H-d/H-d$^1$) ppm. $^{13}$C NMR (CDCl3, 300 MHz) 14.1, 22.7, 26.2, 29.1, 29.3, 29.4, 31.5, 31.9, 46.6, 49.9, 50.8, 61.5, 63.2, 128.1, 128.9, 133.9, 134.7, 162.9, 169.9, 170.8, 191.3 ESI-MS (m/z): 598.5 (M+)$^+$ Compound 8(j)

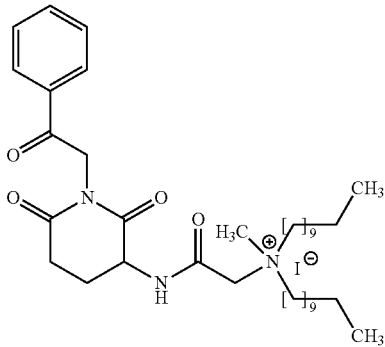

{[2,6-Dioxo-1-(2-oxo-2-phenyl-ethyl)-piperidin-3-ylcarbamoyl]-methyl}-Methyl-diundecyl-ammonium iodide: (8j)

Yellow oil, yield: 68.61%; $^1$H NMR (CDCl$_3$, 300 MHz) δ 9.34 (1H, d, J=8.13 Hz, NH), 7.95 (2H, d, J=7.77 Hz, H-13/H-17), 7.60 (1H, t, J=7.53 Hz, H-15), 7.48 (2H, t, J=7.77 Hz, H-14/H-16), 5.19 (2H, s, H10), 4.84-4.79 (2H, m, H-9), 4.33 (1H, d, J=13.66 Hz, H-6), 3.52-3.50 (4H, m, H-a/H-a$^1$), 3.37 (3H, s, H-e) 3.00-2.94 (1H, m, H-4eq), 2.86-2.77 (1H, m, H-4ax), 2.60-2.49 (1H, m, H-5eq), 2.29-2.25 (1H, m, H-5ax), 1.74-1.71 (4H, m, H-b/H-b$^1$), 1.34-1.24 (36H, m, H-c/H-c$^1$), 0.88. (6H, s, J=6.95 Hz H-d/H-d$^1$) $^{13}$C NMR (CDCl3, 300 MHz) 14.1, 22.7, 26.2, 29.1, 29.3, 29.4, 29.5, 31.5, 31.9, 46.6, 49.9, 50.8, 61.5, 63.2, 128.1, 128.9, 133.9, 134.7, 162.9, 169.9, 170.8, 191.3 ESI-MS (m/z): 626.5 (M+)$^+$ Compound 8(k)

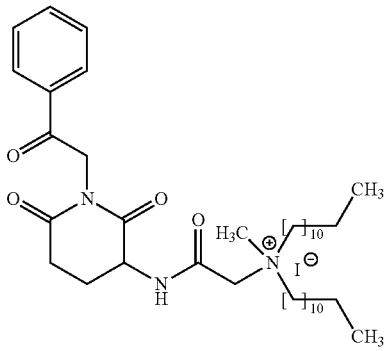

{[2,6-Dioxo-1-(2-oxo-2-phenyl-ethyl)-piperidin-3-ylcarbamoyl]-methyl}-Didodecyl-methyl-ammonium iodide: (8k)

Yellow oil, yield: 70.32%; $^1$H NMR (CDCl3, 300 MHz) δ 9.40 (1H, d, J=8.08 Hz, NH), 7.96 (2H, d, J=7.72 Hz, H-13/H-17), 7.60 (1H, t, J=7.72 Hz, H-15), 7.48 (2H, t, J=7.63 Hz, H-14/H-16), 5.19 (2H, s, H10), 4.86-4.76 (2H, m, H-9), 4.29 (1H, d, J=13.42 Hz, H-6), 3.51-3.49 (4H, m, H-a/H-a$^1$), 3.37 (3H, s, H-e) 3.00-2.96 (1H, m, H-4eq), 2.87-2.77 (1H, m, H-4ax), 2.58-2.52 (1H, m, H-5eq), 2.30-2.27 (1H, m, H-5ax), 1.74 (4H, m, H-b/H-b$^1$), 1.35-1.25 (36H, m, H-c/H-c$^1$), 0.88 (6H, t, J=7.05 H-d/H-d$^1$). $^{13}$C NMR (CDCl3, 300 MHz) 14.1, 22.7, 26.2, 29.1, 29.3, 29.4, 31.5, 31.9, 46.6, 49.9, 50.8, 61.5, 63.2, 128.1, 128.9, 133.9, 134.7, 162.9, 169.9, 170.8, 191.3 ESI-MS (m/z): 654.5 (M+)$^+$ Compound 8(l)

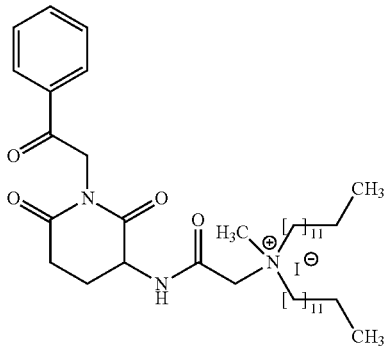

{[2,6-Dioxo-1-(2-oxo-2-phenyl-ethyl)-piperidin-3-ylcarbamoyl]-methyl}-Methyl-ditridecyl-ammonium iodide: (8l)

Yellow oil, yield: 72.0%; $^1$H NMR (CDCl$_3$, 300 MHz) δ 9.34 (1H, d, J=8.28 Hz, NH), 7.94 (2H, d, J=7.55 Hz, H-13/1H-17), 7.60 (1H, d, J=7.18 Hz, H-15), 7.48 (2H, t, J=8.29 Hz, H-14/H-16), 5.19 (2H, s, H10), 4.84-4.79 (2H, m, H-9), 4.32 (1H, d, J=13.92 Hz, H-6), 3.52-3.50 (4H, m, H-a/H-a$^1$), 3.37 (3H, s, H-e) 3.00-2.95 (1H, m, H-4eq), 2.86-2.77 (1H, m, H-4ax), 2.61-2.49 (1H, m, H-5eq), 2.29-2.25 m, H-5ax), 1.74 (4H, m, H-b/H-b$^1$), 1.35-1.24 (4H, q, J=7.41 Hz H-c/H-c$^1$), 0.87-0.85 (6H, t, J=6.25) ppm. $^{13}$C NMR (CDCl3, 300 MHz) 14.2, 22.7, 26.2, 29.1, 29.4, 29.7, 31.5, 31.9, 46.6, 49.9, 50.8, 61.5, 63.2, 128.1, 128.9, 133.9, 134.7, 162.9, 169.9, 170.8, 191.3 ESI-MS (m/z): 682.6 (M+)$^+$ Compound 8(m)

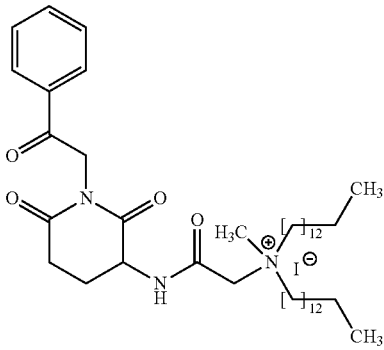

{[2,6-Dioxo-1-(2-oxo-2-phenyl-ethyl)-piperidin-3-ylcarbamoyl]-methyl}Methyl-ditetradecyl-ammonium iodide: (8m)

Yellow oil, yield: 65.3%; $^1$H NMR (CDCl3, 300 MHz) δ 9.25 (1H, d, J=7.84 Hz, NH), 7.95 (2H, d, J=7.57 Hz, H-13/H-17), 7.60 (1H, d, J=7.53 Hz, H-15), 7.41 (2H, t, J=7.91 Hz, H-14/H-16), 5.12 (2H, s, H10), 4.75-4.68 (2H, m, H-9), 4.30-4.20 (1H, d, J=14.19 Hz, H-6), 3.46-3.43 (4H, m, H-a/H-a$^1$), 3.31 (3H, s, H-e) 2.92-2.87 (1H, m, H-4eq), 2.78-2.69 (1H, m, H-4ax), 2.49-2.45 (1H, m, H-5eq), 2.21-2.18 (1H, m, H-5ax), 1.68 (4H, m, H-b/H-b$^1$), 1.27-1.17 (4H, q, J=7.41 Hz H-c/H-c$^1$), 0.81 (6H, t, J=6.48 Hz H-d/H-d$^1$) ppm. $^{13}$C NMR (CDCl$_3$, 300 MHz) 14.2, 22.7, 26.3, 29.1, 29.4, 29.5, 29.6, 29.7, 31.5, 32.0, 46.6, 49.9, 50.8, 61.5, 63.2, 63.3, 128.1, 128.9, 133.9, 134.7, 162.9, 169.9, 170.8, 191.3. ppm. ESI-MS (m/z): 710.6 (M+).

Biological Evaluation

Cell Lines and Culture:

The human cancer cell lines e.g. HepG2 (hepatocellular carcinoma, ATCC® HB-8065™), PC-3 (human prostate cancer cells, ATCC® CRL-1435™), MCF-7 (breast adenocarcinoma, ATCC® HTB-26™), and mouse embryo fibroblasts (NIH/3T3, ATCC® CRL-1658™), used in the present study were obtained from the ATCC (American Type Culture Collection, USA and maintained in RPMI 1640 (Roswell Park Memorial Institute, Merck) with 10% FBS (Merck), supplemented with 1% antibiotic and antimycotic solution (Gibco, USA) at 37° C. in a humidified incubator with 5% CO$_2$. All stock solutions of the compounds were prepared in cell culture grade DMSO (dimethyl sulfoxide) and stored at −20° C. Compounds were diluted in culture media prior to use in experiments. Annexin V-FITC apoptosis detection kits were purchased from Calbiochem. MTT dye was procured from Sigma-Aldrich. All the flow cytometry experiments were performed using a FACScan (Becton Dickinson, Mountain View, Calif.) flow cytometer, equipped with a single 488 nm argon laser.

MTT Assay for Cell Viability:

Cell viability was assessed by MTT assay, which is based on the reduction of MTT by mitochondrial dehydrogenases of viable cells to form a purple formazan product. Briefly, cells (5-6×10$^3$/well) were plated in 96 well plates. After incubating overnight, the cells were treated with six different concentrations (100, 50, 20, 10, 5, 2.5, 1.25 µM) in triplicates with the cationic lipidated cordiarimide and intermediates for 48 h. Subsequently, 10 µL of MTT (10 mg/mL) was added to each well and incubated for 3 h. The MTT formazan formed by viable cells was dissolved in 100 µL of DMSO and shaken for 10 min. The absorbance was measured on an ELISA reader. Each test was repeated at least three times. The concentration of the compound which gives the 50% growth inhibition value corresponding to IC$_{50}$, was calculated using GraphPad prism 5 software. In the present invention we have screened 26 lipidated cordiarimides and the results are described in table 1. Among the tested hybrids, neutral compounds 7e-7 g (table 1) are moderately active and cationic cordiarimide compounds 8f-8k (table 1) exhibited potential antiproliferative activity towards cancer cell lines and especially 8k has shown very good selective anticancer activity in cancer cell lines PC-3, HepG2 and MCF-7 cells with IC-50 values 5.6, 1.8, 26.3 µM, respectively. This indicates that lipid conjugation endowed phenomenal anticancer activity to inactive cordiarimide A reported by Kittakoop et al.

Figure 1:
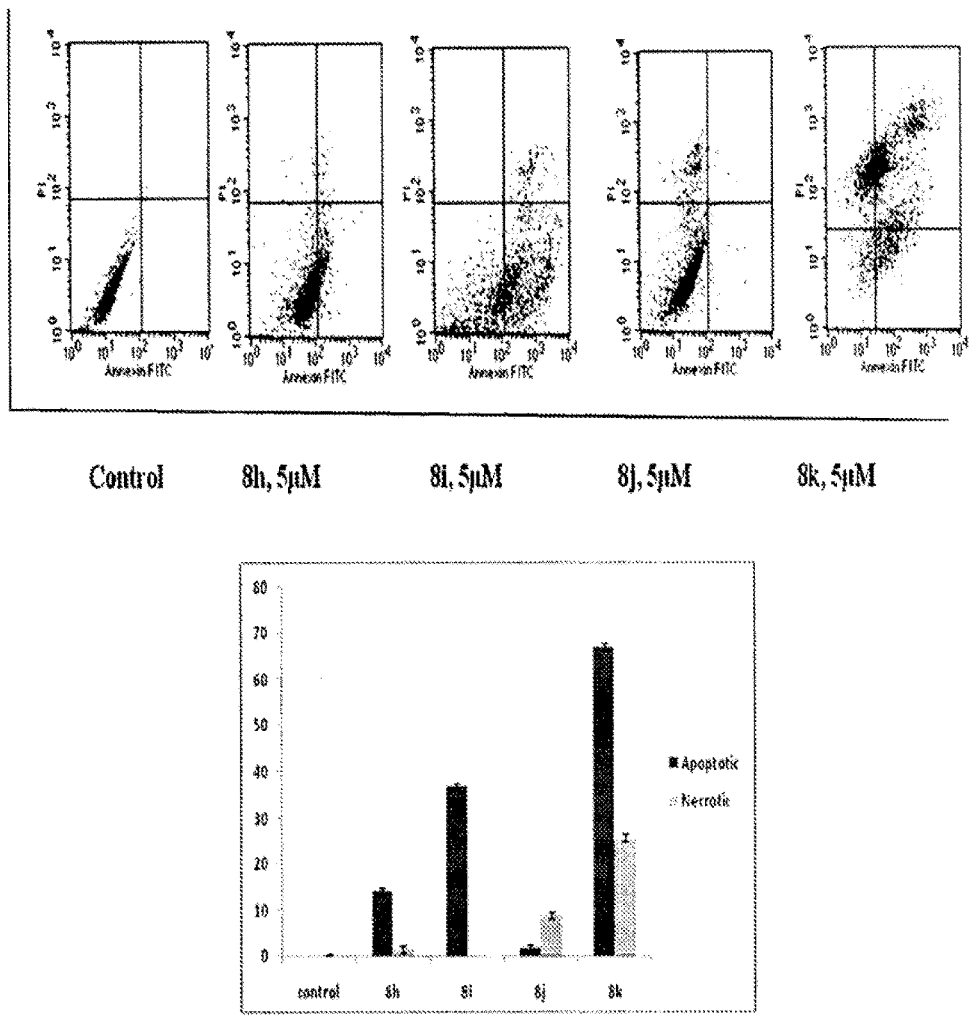
FIG. 1: illustrates analysis of apoptosis induction by cationic lipid-cordiarimide hybrids 8h, 8i, 8j, 8k in the HepG2 cell line at 5 μM concentrations. Cells were treated with different concentrations of above for 24 h and apoptosis was analyzed using annexin V and propidium iodide double staining by flow cytometry.

Apoptosis Studies:

Quantitation of apoptotic cells by annexin V staining was carried out according to the manufacturer's instructions. Briefly, cells (5×10$^5$ cells/well) were seeded in 6 well plates and treated with 5 µM of 8h-8k for 24 h. After incubation, cells were washed with PBS and stained with 1.25 µL of annexin V-FITC and 10 µL of media binding reagent and incubated for 20 min. After that 10 µL of PI was added and samples were analyzed using a flow cytometer. Annexin V-FITC was analyzed using excitation and emission settings of 488 nm and 535 nm (FL-1 channel); PI, 488 nm and 610 nm (FL-2 channel). Debris and clumps were gated out using forward and orthogonal light scatter. Each experiment was repeated two times independently. Results are illustrated in FIG. 1 and the percentage of Annexin-V/PI positive cells increased gradually from 20 to 70% after 24 h of treatment (FIG. 1). These results indicated that the active compounds 8h-8k induced apoptosis in HepG2 cells.

Cell Cycle Analysis:

For cell cycle distribution studies after treatment with different molar concentrations of 8i and 8k, HepG2 cells were fixed overnight in 70% ethanol, rehydrated in PBS with ribonuclease A (100 µg/ml) and Triton-X (1%) for 30 min at room temperature then PI (at 50 µg/ml) was added and incubated in the dark for 30 min and analyzed with a flow cytometer. Experiments were repeated two times independently. Results depicted in FIGS. 2 and 24 h treatment of compound 8i did not altered cell cycle progression of HepG2 cells except for the induction of apoptosis. Whereas 8k treatment resulted in a significant accumulation of cells in G0/G1 phase, characteristic of a G0/G1 phase arrest (FIG. 2B).

Figure 3:
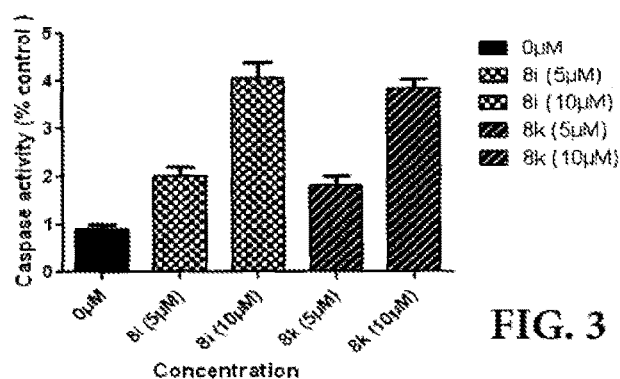
FIG. 3: illustrates dose dependent caspase-3 activation by cationic lipid-cordiarimide hybrid 8i & 8k in HepG2 cells: $1 \times 10^5$ cells/well with 70-80% confluence were grown and treated with 0, 5 and 10 μM of compounds 8i & 8k for 24 h. Colorimetric determination of general caspase was done as described in materials and methods each data point is the representation of triplicate treatments.

Caspase-3 Activation Assay:

The activity of caspase-3 was determined using a caspase-3 colorimetric assay kit (Sigma Aldrich) according to the manufacturer's protocol. Briefly, HepG2 cells (1×10$^6$ cells/well) were treated with 5 and 10 µM of 8i and 8k for 24 h. The cells were harvested and lysed by addition of lysis buffer. Cell lysates were mixed with colorimetric substrate (Ac-DEVD-pNA) and incubated at 37° C. in the dark for 4 h. The absorbance was measured at 405 nm in an ELISA reader. Caspase-3 activity was expressed as the change of the activity compared to the control (FIG. 3). Both the compounds 8i and 8k activated the caspase-3 in HepG2 cells dose dependently (FIG. 3) and this confirms that the apoptosis induction is due to caspase-3 activation by compounds 8i and 8k in HepG2 cells.

Figure 7:
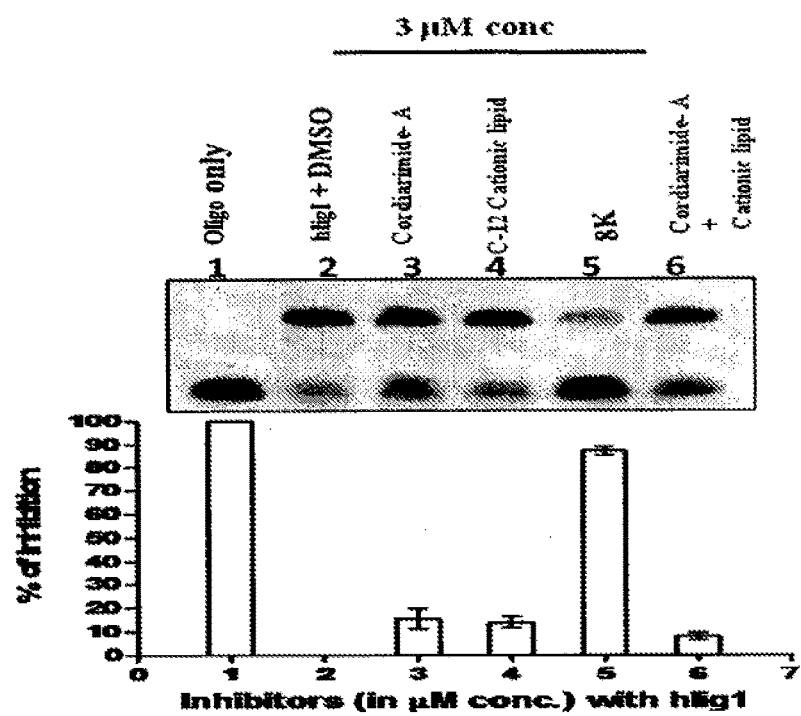
FIG. 7: Describe the comparative inhibition of ligation activity of and lipid hybrid 8k, Cordiarimide A and the twelve chain length cationic lipid and their physical mixture.

Ligation Assay:

The ligation assay was done strictly following the assay protocol described in Xi Chen et. al, Cancer Res 2008; 68(9):3169-3177. The DNA molecules 52 mer (5'-3'), 28-mer (5'-3') and 34-mer (5'-3') were used to construct a double stranded nicked substrate for the ligase enzyme (FIG. 4). The 34-mer oligo was labelled with 32P-AMP to form a substrate for ligase and to form a ligase-AMP intermediate. During ligation, the ligase would transfer the AMP to the nick forming a phosphodiester bond and seal the nick. The ligated DNA molecule would be larger in size and run higher up on a 7% Urea-containing denaturing acrylamide gel. If an inhibitor is added to the reaction mixture prior to the addition of ligase, this would lead to an inhibition of ligation and a corresponding loss of labelled ligated product in the gel. We would then be able to calculate the percentage of inhibition of ligation by estimating the amount of ligated product in the lane with no inhibitor and comparing it with the lanes containing different inhibitor molecules or with the same inhibitor molecule at different concentrations. Such a comparison done with 8f to 8m revealed that disclosed 8k (FIG. 4) was the most prolific inhibitor of ligation compared to the other compound. It was also revealed that the 8k was a specific inhibitor of ligase I function, with only marginal ligase III inhibition (of 30%) at concentrations that kill HepG2 cells, and has no effect on ligase IV activity even at higher concentrations (FIGS. 5A and B). 8k exhibited selective DNA ligase I inhibition whereas the synthesized cationic lipid cordiaroimide hybrids (8a-8j & 8l, 8m) which are structurally very similar to 8k did not elicit any DNA ligase I inhibition (FIG. 4). Moreover, parent molecules Cordiarimide A and the twelve chain length cationic lipid and their physical mixture also did not show any ligation inhibition (FIG. 7).

In the present invention we have shown the development of novel selective anticancer agents and for the first time we are demonstrating a novel phenomena that chain length can play a vital role in the molecular targeting of small molecules.

The slight overlap of ligase III inhibition may actually be beneficial for cancer therapy given reports that ligase III can somewhat take over the activity of ligase I in its absence. While the complete inhibition of ligase I activity will ensure a block to replication of cancer cells, the partial ligase III block ensures that alternate repair pathways are also blocked. The residual ligase III activity however could ensure DNA repair in non-replicating cells of the body, hence eliminating side-effects. Hence a patient treated at concentrations of 8k that completely inhibit both ligase I and ligase III activity will completely block replication of cancer cells at the beginning of treatment. Thereafter, for a long term treatment, the patients may be shifted to lower dosage regimens that block only the ligase I activity while still allowing some residual ligase III activity. This will ensure that normal non-replicating cells in the body can carry out repair activities normally and not be killed by the inhibitor.

Figure 6A:
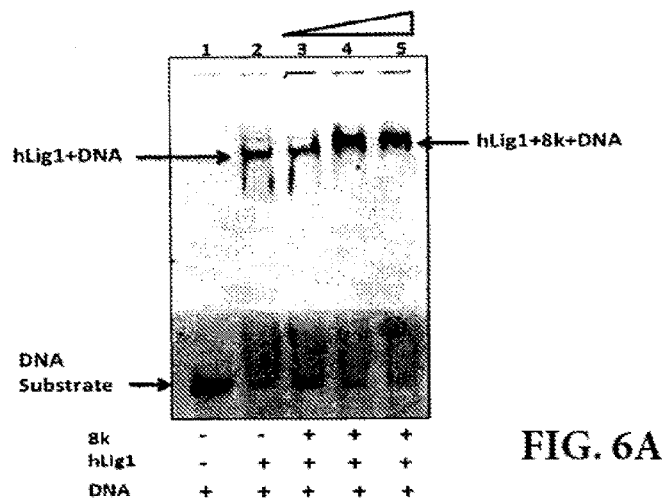
FIG. 6A: Electrophoretic mobility shift assay: Effect of 8k at 25, 50 and 100 μM concentrations (lanes 3-5) on hLig1 (10 pmol) binding to DNA substrate (1 pmol) labelled with FAM. Lanes 4 and 5 show a mobility shift above the hLig1-DNA complex (lane 2) and points to an un-competitive mode of inhibition due to formation of a super-complex of hLig1-8k-DNA.
Figure 6B:
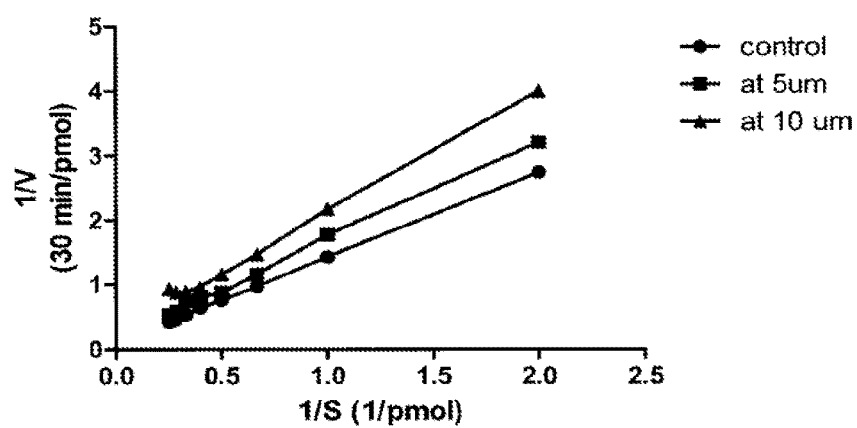
FIG. 6B: Kinetic analysis of ligation inhibition by 8k is performed to validate the mode of inhibition of ligation by 8k and the result indicate that 8k inhibits the hLig1 un-competitively.

Electrophoretic Mobility Shift Assay (EMSA):

EMSA was performed as described in Xi Chen et. al, Cancer Res 2008; 68(9):3169-3177 with some modifications, for the interaction study between 8k and hLig1. Of the three oligos used to construct the DNA substrate, one was a 5'-FAM labelled 27-mer oligo with a dideoxy modified 3' end. Other two oligos of 25-mer and 52-mer were used. These oligos were annealed to obtain a non-ligatable nicked DNA substrate which the ligase enzyme can recognize and bind to, but cannot ligate or release from it. Ligase binding to non ligatable nicked DNA substrate would lead to an increase in molecular weight and hence a shift in signal from bottom of gel (free DNA) to top of gel (ligase bound DNA) (lane 2 of FIG. 6A). Lanes 3-5 (FIG. 6A) contain increasing concentrations of the inhibitor. A shift in signal is seen is lanes 3-5. This shift in the ligase-DNA complex can occur only if the inhibitor binds to the complex of hLig1+DNA and increases the size of the complex. If inhibitor binds to ligase alone, then we would expect fewer signals in lanes 3-5. But since we see an increase in intensity of signal as well as a super-shift in the signal, we can reliably say that the inhibitor binds to the DNA-ligase complex and not separately to either DNA or ligase. This points to an un-competitive mode of inhibition of 8k (FIG. 6A). The mode of inhibition was further validated by enzyme kinetics study as shown in FIG. 6B.

Kinetic Analysis of Ligation Inhibition by 8k:

Significantly, enzyme kinetics was performed as described in Xi Chen et. al, Cancer Res 2008; 68(9):3169-3177, for validation of the mode of inhibition of ligation by 8k. We measured the kinetics of hLig1 mediated ligation in the absence are presence of 8k at 5 and 10 μM concentrations and drew Lineweaver-Burk plots (FIG. 6B). The resulting plot clearly demonstrates that increasing concentration of 8k leads to decrease in the value of Vmax and Km, which conclusively prove that 8k inhibits the hLig1 un-competitively.

Figure 6C:
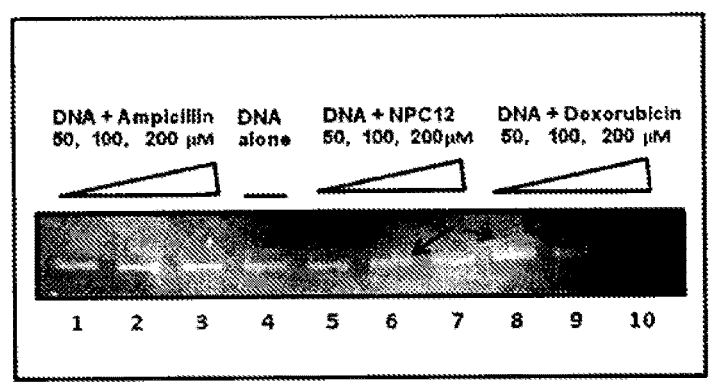
FIG. 6C: DNA intercalation assay was performed to determine the DNA binding ability of 8k. Ampicillin was used as negative control (lanes 1-3) and doxorubicin was used as positive control (lanes 8-10).

DNA Intercalation Assay:

Since there are multiple modes of inhibition of ligase activity, we wanted to determine whether 8k inhibited ligation by direct inhibition alone or through other means as well such as DNA intercalation. DNA intercalation assay was performed as described by Furlan et al., *Biotechnol. Lett.* 2002, 24, 1807-1813. We incubated 100 ng of linearized plasmid pUC18 DNA with increasing concentrations (50, 100, 200 μM) of Doxorubicin (positive control), ampicillin (negative control), and 8k for 30 minutes at 37° C. Reaction products were resolved on a 1% agarose gel at 5.3 V/cm. Gel was visualized by ethidium bromide staining. As seen in lanes 5-7 (FIG. 6C), no appreciable intercalation was observed with 8k when compared to doxorubicin up to 100 μM concentration. Therefore the EMSA, the intercalation assay and the kinetic analysis of inhibitor 8k conclusively prove that 8k binds to the ligase-DNA complex rather than binding to either ligase or DNA alone.

Comparison of Biological Activity of Test Compounds with the Parent Compounds:

Biological activity of test compounds was compared With the cordiarimide compounds and its side chains. Three quaternary lipid chains bearing carbon chain length eight, ten and twelve (8g, 8i, 8j) were synthesized and tested for their anticancer activity against the HepG2 cell line and the results are given in Table-2 below. The hybrid compounds are more active than the two parent molecules namely Cordiarimide A and Cationic lipid chains. Interestingly, the amount of activity and selectivity is highly dependent upon chain length. Eight (8g) and ten (8i)-carbon chain containing compounds showed very good anticancer activity without selectivity. Interestingly, the twelve carbon chain bearing compound (8j) showed selective anticancer activity in liver (HepG2) cancer cells (Table 2) and 8k showed inhibition of DNA ligase I activity (FIG. 4, FIGS. 5A & B). Hence, DNA ligase-I could be the possible target for the selective anti-proliferative activity of 8k.

TABLE 2

| Cordiarimide A and IC$_{50}$ values in (μM) HepG2 cells | Cationic Lipid chains and their IC$_{50}$ values (μM) in HepG2 cells | Hybrid compounds and their IC$_{50}$ values (μM) in HepG2 cells |
|---|---|---|
| 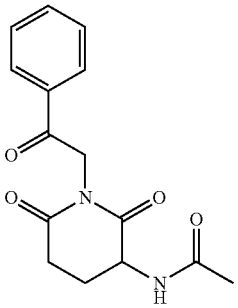 (Inactive) | 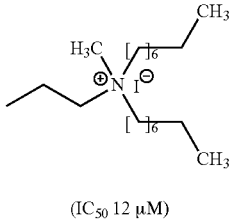 (IC$_{50}$ 12 μM) | 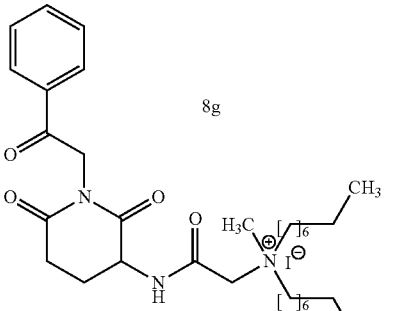 8g (IC$_{50}$ 3.42 μM) |
| | 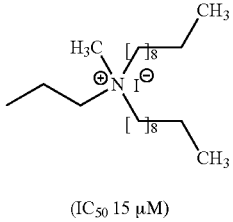 (IC$_{50}$ 15 μM) | 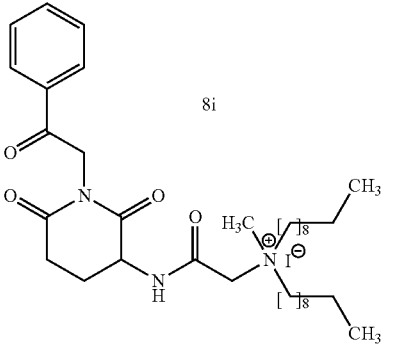 8i (IC$_{50}$ 3.07 μM) |
| | 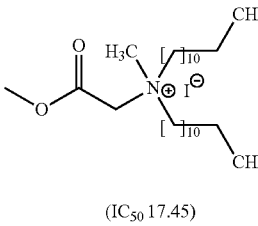 (IC$_{50}$ 17.45) | 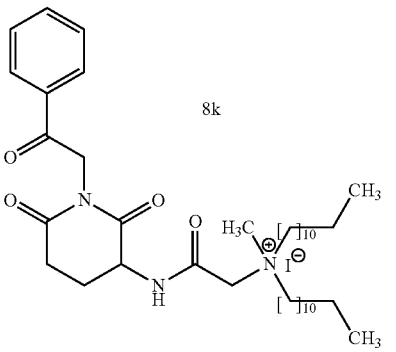 8k (IC$_{50}$ 1.872 μM) |

Advantages of the Present Invention

1. Development of a new glutarimide based anticancer agents for hepatocellular and prostate cancers.
2. Discovery of a highly potent and novel selective human DNA Ligase-I inhibitor.
3. Identification of the novel phenomenon that the cationic lipid with twelve carbon chains is the only perfect partner for cordiarimide A in order to elicit selective anticancer activity and DNA Ligase-I inhibitory potential.

The invention claimed is:
1. A cationic lipid cordiarimide hybrid compound of formula I formula I

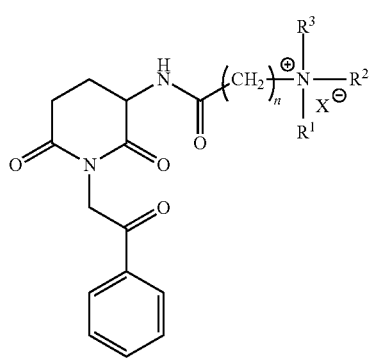

wherein
each of $R^1$ and $R^2$ is independently hydrogen or a lipophilic moiety and $R^1$ and $R^2$ are not hydrogen at the same time,
$R^3$ is hydrogen or alkyl,
n is an integer between 1 and 7, and
X is chlorine, bromine or iodine,
wherein the lipophilic moiety is selected from the group consisting of $C_{2-22}$ alkyl, and mono-, di- and tri-unsaturated alkenyl.

2. The compound of claim 1, wherein the compound of formula I is:
  a) {[2,6-Dioxo-1-(2-oxo-2-phenyl-ethyl)-piperidin-3-yl-carbamoyl]-methyl}-diethyl-methyl-ammonium iodide (8a);
  b) Dipropylamm{[2,6-dioxo-1-(2-oxo-2-phenyl-ethyl)-piperidin-3-ylcarbamoyl]-methyl}-methylammonium iodide (8b);
  c) Dibutyl-{[2, 6-dioxo-1-(2-oxo-2-phenyl-ethyl)-piperidin-3-ylcarbamoyl]-methyl}-methyl-ammonium iodide (8c);
  d) {[2,6-Dioxo-1-(2-oxo-2-phenyl-ethyl)-piperidin-3-yl-carbamoyl]-methyl}-Methyl-dipentyl-ammonium iodide (8d);
  e) {[2,6-Dioxo-1-(2-oxo-2-phenyl-ethyl)-piperidin-3-yl-carbamoyl]-methyl}-dihexyl-methyl-ammonium iodide (8e);
  f) {[2,6-Dioxo-1-(2-oxo-2-phenyl-ethyl)-piperidin-3-yl-carbamoyl]-methyl}-diheptyl-methyl-ammonium iodide (8f);
  g) {[2,6-Dioxo-1-(2-oxo-2-phenyl-ethyl)-piperidin-3-yl-carbamoyl]-methyl}-methyl-dioctyl-ammonium iodide (8g);
  h) {[2,6-Dioxo-1-(2-oxo-2-phenyl-ethyl)-piperidin-3-yl-carbamoyl]-methyl}-methyl-dinonyl-ammonium iodide (8h);
  i) Bis-decyl-{[2,6-dioxo-1-(2-oxo-2-phenyl-ethyl)-piperidin-3-ylcarbamoyl]-methyl}-methyl-ammonium iodide (8i);
  j) {[2,6-Dioxo-1-(2-oxo-2-phenyl-ethyl)-piperidin-3-yl-carbamoyl]-methyl}-methyl-diundecyl-ammonium iodide (8j);
  k) {[2,6-Dioxo-1-(2-oxo-2-phenyl-ethyl)-piperidin-3-yl-carbamoyl]-methyl}-didodecyl-methyl-ammonium iodide (8k);
  l) {[2,6-Dioxo-1-(2-oxo-2-phenyl-ethyl)-piperidin-3-yl-carbamoyl]-methyl}-Methyl-ditridecyl-ammonium iodide (8l); or
  m) {[2,6-Dioxo-1-(2-oxo-2-phenyl-ethyl)-piperidin-3-yl-carbamoyl]-methyl}-Methyl-ditetradecyl-ammonium iodide (8m).

3. A process for the preparation of compounds of formula I of claim 1, wherein said process comprises the steps of:
  (a) Boc protection of free amine group of amino acid L-Glutamine to obtain compound 1, followed by cyclization of (Boc)-Glutamine using DCC, NHS to generate compound 2;
  (b) arylation of imide N—H group of the compound 2, obtained in step (a) using phenacyl bromide in the presence of a base $K_2CO_3$, at a temperature ranging from 25° C. to 80° C. for a period ranging from 8 to 12 hours to obtain compound 3, followed by Boc deprotection to obtain amine intermediate compound 4;
  (c) reacting compound 4 obtained from step (b) with Boc-glycine to produce the subsequent Boc glycine glutarimide intermediate compound 5;
  (d) deprotecting compound 5 obtained from step (c) to obtain glycine conjugated free amine compound 6;
  (e) reacting compound 6 obtained from step (d) with an alkyl bromide to form a compound 7 followed by quaternization of compound 7 with an alkyl halide to obtain a compound of formula I;
wherein compounds 1-7 have the following structures:

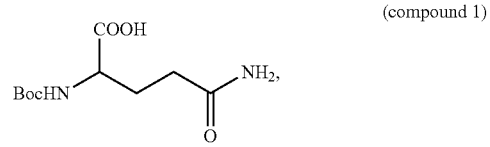
(compound 1)

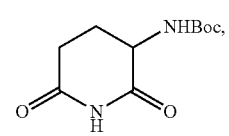
(compound 2)

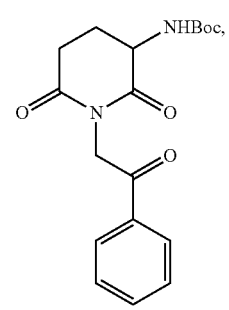
(compound 3)

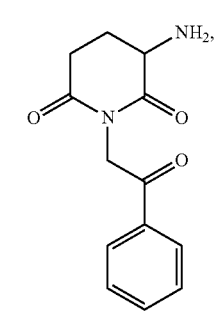
(compound 4)

(compound 5) 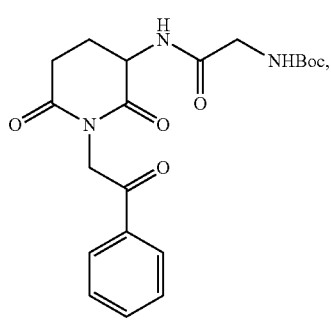

(compound 6) 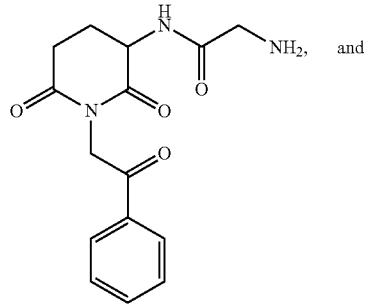
and (compound 7) 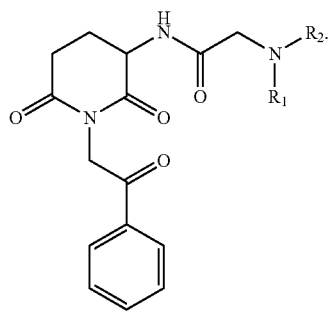

4. The process of claim 3, wherein the alkyl bromide in step (e) has an aliphatic hydrocarbon chain length selected from 2-22 carbon atoms.

5. The process of claim 3, wherein the alkyl halide for quaternization has an aliphatic hydrocarbon chain length selected from 1-5 carbon atoms.

6. The process of claim 3, wherein the quaternization of the compound 7 obtained from step (e) is carried out at a temperature in the range of 10° C. to 40° C.

7. A pharmaceutical composition, comprising the compound of formula I along with a pharmaceutically acceptable additive or carrier.

8. A method of inhibiting DNA ligase in a cell, comprising contacting the cell in vitro with an effective amount of the compound of claim 1.

9. A method for treating cancer, comprising administering to a patient in need thereof an effective amount of the pharmaceutical composition of claim 7;
wherein the cancer is breast cancer, liver cancer, or prostate cancer.

10. The compound of claim 1, wherein n is 1.

11. The compound of claim 10, wherein $R^3$ is H or $CH_3$.

12. The compound of claim 11, wherein X is iodine.

13. The compound of claim 12, wherein each of $R^1$ and $R^2$ is independently $C_{2-14}$ alkyl.

14. The compound of claim 13, wherein each of $R^1$ and $R^2$ is independently $C_{7-12}$ alkyl.

* * * * *